Figure 1:
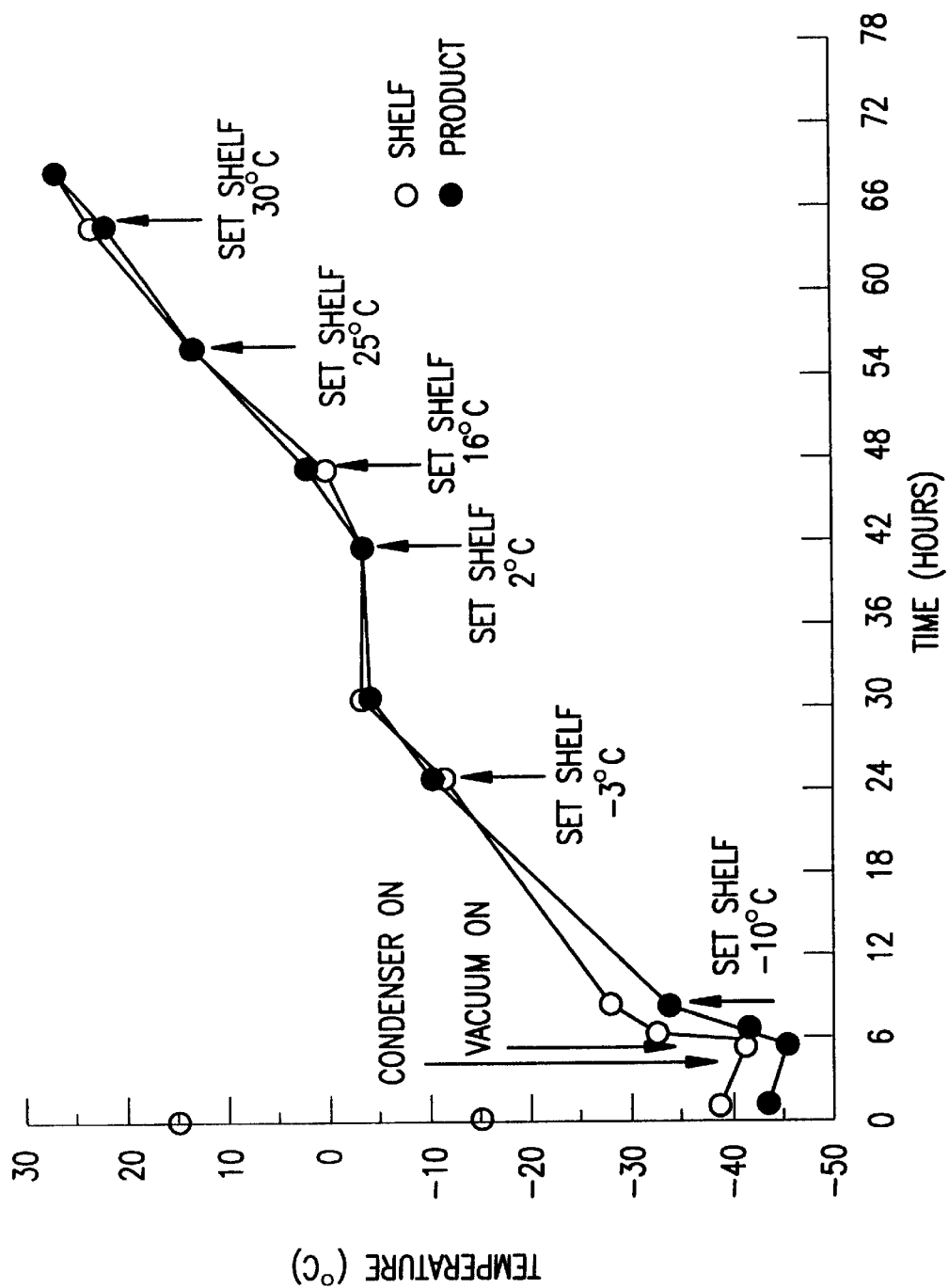

United States Patent [19]

Ultee et al.

[11] Patent Number: 5,942,210

[45] Date of Patent: Aug. 24, 1999

[54] METHODS FOR LYOPROTECTING A MACROMOLECULE USING TRICINE

[75] Inventors: Michiel E Ultee, Belle Meade; Charlotte A Burton, Brick, both of N.J.

[73] Assignee: Cytogen Corporation, Princeton, N.J.

[21] Appl. No.: 08/339,865

[22] Filed: Nov. 15, 1994

[51] Int. Cl.$^6$ .......................... A61K 51/04; A61K 38/00; C07F 5/00; C07K 16/00

[52] U.S. Cl. .................... 424/1.69; 530/391.5; 530/300; 530/388.85; 530/395; 514/8; 562/575; 252/73; 534/10; 534/14

[58] Field of Search ................................. 424/1.53, 1.69, 424/9.34; 534/10, 14; 530/391.5, 300, 388.85, 395; 514/8; 34/284; 252/73; 562/575

[56] References Cited

U.S. PATENT DOCUMENTS

| | | |
|---|---|---|
| 3,940,943 | 3/1976 | Sikes et al. . |
| 4,287,362 | 9/1981 | Yokoyama et al. . |
| 4,390,517 | 6/1983 | O'Brien et al. . |
| 4,732,864 | 3/1988 | Tolman . |
| 4,741,900 | 5/1988 | Alvarez et al. . |
| 4,806,343 | 2/1989 | Carpenter et al. ...................... 424/450 |
| 5,032,521 | 7/1991 | White et al. . |
| 5,162,504 | 11/1992 | Horoszewicz . |
| 5,196,510 | 3/1993 | Rodwell et al. . |
| 5,242,679 | 9/1993 | Fritzberg et al. ........................ 424/1.1 |
| 5,326,856 | 7/1994 | Coughlin et al. . |
| 5,350,837 | 9/1994 | Bridger et al. ............................ 434/14 |

FOREIGN PATENT DOCUMENTS

| | | |
|---|---|---|
| 0 188 256 | 7/1986 | European Pat. Off. . |
| 0 569 132 | 10/1993 | European Pat. Off. . |
| WO 91/04056 | 4/1991 | WIPO . |
| WO 93/21151 | 10/1993 | WIPO . |
| WO 94/10149 | 5/1994 | WIPO . |
| WO 94/18318 | 8/1994 | WIPO . |

OTHER PUBLICATIONS

Ashwood–Smith et al. "Cryoprotection of Mammalian Cells in Tissue Culture with Pluronic Polyols", Cryobiology, 10, 502–504 (1973). Without Month.

BMC Biochemicals 1994 Catalog, Protein Research Products, Catalog No. 1420 429/1047 825. Without Month.

Hnatowich et al., 1993, "Directly and Indirectly Technetium–99m–Labeled Antibodies—A Comparison of In Vitro and Animal In Vivo Properties", *J. Nucl. Med.* 34/1:109–119. Without Month.

Rea et al., 1993, "A novel method for controlling the pepsin digestion of antibodies", *J. Immunol. Methods* 157:165–173. Without Month.

CALBIOCHEM Biochemical/ Immunological 1992 Catalog, Catalog Nos. 324714 and 324715. Without Month.

Rosenstraus et al., 1991, "Immunohistochemical and Pharmacokinetic Characterization of Site–specific Immunoconjugate 15A8–Glycyl–tyrosyl–(N–ϵ–diethylenetriamine Pentaacetic Acid)–lysine Derived from Anti–Breast Carcinoma Monoclonal Antibody 15A8", *Cancer Research* 51:5744–5751. Without Month.

Carpenter et al., 1991, "Interaction of Stabilizing Additives with Proteins during Freeze–Thawing and Freeze–Drying", *Develop. Biol. Standard* 74:225–239. Without Month.

Thakur et al., 1991, "Technetium–99m Labeled Monoclonal Antibodies: Evaluation of Reducing Agents", *Int. J. Rad. Appl. Instrum.* [B] 18/2:227–233. Without Month.

Schwartz et al., 1991, "Preparation of Hydrazine–Modified Proteins and Their Use for the Synthesis of $^{99m}$Tc–Protein Conjugates", *Bioconjugate Chem.* 2:333–336. Without Month.

Fritzberg et al., 1988, "Specific and stable labeling of antibodies with technetium–99m with a diamide dithiolate chelating agent", *Proc. Natl. Acad. Sci. USA* 85:4025–4029. Without Month.

Arano, 1987, "Technetium–99m–Labeled Monoclonal Antibody with Preserved Immunoreactivity and High In Vivo Stability", *J. Nucl. Med.* 28/6:1027–1033. Without Month.

Arano, 1986, "Synthesis and evaluation of a new bifunctional chelating agent for $^{99m}$Tc labelling proteins: p–carboxyethylphenylglyoxal–di(N–methylthiosemicarbazone)", *Int. J. Nucl. Med. Biol.* 12/6:425–430. Without Month.

White et al., 1985, "Two Monoclonal Antibodies Selective for Human Mammary Carcinoma", *Cancer Research* 45:1337–1343. Without Month.

Pinkerton et al., 1985, "Bioorganic Activity of Technetium Radiopharmaceuticals", *J. Chem. Ed.* 62/11:965–973. Without Month.

Robbins, 1984, *Chromatography of Technetium–99$^m$Radiopharmaceuticals: A Practical Guide.*, Society of Nuclear Medicine, NY, NY, p. 1–35. Without Month.

Rhodes and Burchiel, 1983, "Radiolabeling of Antibodies with Technetium–99m", In: *Radioimmunoimaging and Radioimmunotherapy,* Burchiel and Rhodes (Eds.), Elsevier Science Pub. Co., Inc., New York, pp. 207–222. Without Month.

Rhodes et al., 1983, "$^{99m}$Tc–Labeling and Acceptance Testing of Radiolabeled Antibodies and Antibody Fragments", In: *Tumor Imaging* Chapter 12, Burchiel and Rhodes (Eds.), Masson, New York, pp. 111–123. Without Month.

Huang, 1980, "Detection of Bacterial Endocarditis with Technetium–99m–Labeled Antistaphyloccal Antibody", *J. Nucl. Med.* 21/8:783–786. Without Month.

MacKenzie, 1977, "The Physico–Chemical Basis for the Freeze–Drying Process", *Develop. Biol. Standard* 36:51–67. Without Month.

Good et al., 1966, "Hydrogen Ion Buffers for Biological Research" *Biochemistry* 5/2: 467–477. Without Month.

MacKenzie, 1975, "Collapse during freeze drying–qualitative and quantitative aspects", In:*Freeze Drying and Advanced Food Technology,* Chapter 19, Goldblith et al., (Eds.), Academic Press, NY) pp. 277–307. Without Month.

*Primary Examiner*—Gary E. Hollinden
*Assistant Examiner*—Michael G. Hartley
*Attorney, Agent, or Firm*—Pennie & Edmonds LLP

[57] ABSTRACT

This invention relates to lyoprotection agents for protecting macromolecules during lyophilization or freeze-drying. In particular, methods for use of these lyoprotectants in conjugate formulations are disclosed. Additionally, this invention describes lyophilized instant kit formulations for the radiolabeling of pharmaceuticals and/or macromolecules.

8 Claims, 11 Drawing Sheets

METHODS FOR LYOPROTECTING A MACROMOLECULE USING TRICINE

TABLE OF CONTENTS

1. FIELD OF THE INVENTION
2. BACKGROUND OF THE INVENTION
3. SUMMARY OF THE INVENTION
4. BRIEF DESCRIPTION OF THE FIGURES
5. DETAILED DESCRIPTION OF THE INVENTION
   5.1. NOVEL LYOPROTECTANTS
   5.2. ONE POT LYOPHILIZED KIT
      5.2.1. CHEMICAL REDUCING AGENT
      5.2.2. TRANSCHELATOR
      5.2.3. LINKER MOLECULE
      5.2.4. TARGETING MOLECULE
      5.2.5. ONE POT METHOD FOR PREPARING LYOPHILIZED FORMULATION AND KIT
6. EXAMPLES
   6.1. TRICINE AS A LYOPROTECTANT
   6.2 $^{99m}$Tc RADIOCONJUGATE PREPARED USING THE ONE POT LYOPHILIZED KIT
      6.2.1 $^{99m}$Tc INCORPORATION USING THE LYOPHILIZED INSTANT KIT OF THE INVENTION
      6.2.2 LONG TERM STABILITY OF LYOPHILIZED MIXTURE
      6.2.3 STANNOUS STABILITY
      6.2.4 NON-TOXICITY OF TRICINE
      6.2.5 IN VIVO CLEARANCE RATES: COMPARISON BETWEEN A LIQUID FORMULATION AND A FORMULATION PREPARED USING THE PRESENT LYOPHILIZED KIT
   6.3 $^{99m}$Tc LABELING OF CYT-421
   6.4 ONE POT FORMULATION OF CYT-421
   6.5 $^{99M}$Tc LABELING OF CYT-422
   6.6 ONE POT FORMULATION OF CYT-422

1. FIELD OF THE INVENTION

The present invention relates generally to methods and improved compositions for the formulation of macromolecule pharmaceuticals, particularly radiopharmaceuticals. More particularly the invention relates to novel compositions for a ready-to-use kit, the contents of which may be rapidly and facilely combined with a radioisotope, to yield a radiopharmaceutical. The kit components are formulated through lyophilization of a mixture of (1) a chemical reducing agent to lower the oxidation state of a radioisotope, (2) a transchelator which can hold the radioisotope in a reduced oxidation state, (3) a linker which can conjugate to a macromolecule which is a targeting molecule, such as an antibody, etc., and to the radioisotope in the reduced oxidation state to form a radioconjugate, and (4) a targeting molecule, which can deliver the radioconjugate to the desired biological tissue. In a preferred embodiment, the linker and the targeting molecule are covalently linked, thus forming a conjugate.

The present invention further relates to methods for lyoprotection of macromolecules or macromolecular compositions which entail mixing the macromolecule or composition containing the same with a lyoprotectant such as tricine, N-[tris(hydroxymethyl)methyl]glycine.

2. BACKGROUND OF THE INVENTION

Radioisotopes may be introduced into the human body both for purposes of imaging and for purposes of therapy. In either case, it is frequently desirable that the radioisotope be delivered to a specific location within the human body, such as a particular organ or a tumor. One radioisotope which is particularly well-suited for imaging applications is $^{99m}$Tc, which has a half-life of 6 hours, a highly abundant, single γ-ray with an energy of 140 keV, and low tissue deposition of ionizing radiation [Rhodes, B. A. and Burchiel, S. W., In: Radioimmunoimaging and Radioimmunotherapy, Burchiel and Rhodes (Eds.), Elsevier, N.Y., 1983, p. 207]. An important objective is to get the Tc to a specific location in the body. This objective is obtained by combining the Tc with a biological molecule which will concentrate at a particular location within the body.

Currently, there are two general methods of attaching radioisotopes like Tc to biological molecules, nominally termed "direct" and "indirect" labeling [Hnatowich, D. J. et al., 1993, J. Nucl. Med. 34:109–119]. In direct labeling, the radioisotope is combined directly with a biological molecule, or with a chemically reduced biological molecule. Direct labeling of proteins by $^{99m}$Tc can lead to radiochemical impurities. This is undesirable for imaging purposes, because radiochemical impurities which do not concentrate at the desired biological target will lead to a loss of imaging contrast. A direct chemical pretreatment of the protein can provide sites on the biological molecule at which radioisotope can attach. For example, in the case of labeling with $^{99m}$Tc, Rhodes and coworkers found that $Sn^{+2}$ could directly interact with the biological molecule, e.g., a protein, to form sites on the biological molecule at which technetium ions could bind [Rhodes, B. A. and Burchiel, S. W., In: Radioimmunoimaging and Radioimmunotherapy, Burchiel and Rhodes (Eds.), Elsevier, N.Y., 1983, p. 207]. However, the direct labeling approach may lead to relatively weak bonds between Tc and biological molecule, such that Tc can be lost through transchelation processes, thereby reducing radiospecificity [Hnatowich, D. J. et al., 1993, J. Nucl. Med. 34:109–119]. Additionally, direct labeling protocols can alter the specificity of the biological molecule as compared to those not subjected to such protocols, thereby decreasing the amount of the labeled biological molecule actually reaching the desired target.

In the second approach to labeling, termed the "indirect" approach, one adds, to the biological molecule, an entity which will hold the radioisotope. This entity is termed a linker molecule, and must be capable of binding to both the biological molecule, frequently termed the targeting molecule, and to the radioisotope. In some applications, the biological molecule may be chemically modified to receive the linker molecule. When the linker molecule is combined to the targeting molecule, the resultant complex is termed a conjugate molecule. For example, if the biological molecule is an antibody, the resultant complex is termed an immunoconjugate molecule. When a radioisotope is subsequently combined, the resultant molecule is a radioconjugate or in the case of an antibody, a radioimmunoconjugate. Preferably, the linker molecule is conjugated to the biological molecule before the radioisotope is complexed to the linker molecule.

In the specific cases of $^{99m}$Tc (used for imaging) and $^{186}$Re, $^{188}$Re, and $^{189}$Re (used for therapy), the readily available radioconjugate complexes require that the radioisotope be in a low, or chemically reduced, oxidation state. Radioisotopes of Re and Tc are typically available commercially in high oxidation states (e.g., $Re^{+7}$ or $Tc^{+7}$ in $TcO_4^-$ [Pinkerton, T. C. et al., 1985, J. Chem. Ed. 62:966–973]. Chemically reducing the radioisotope to a lower oxidation state, and maintaining that lower oxidation state prior to formation of the radioisotope/biological molecule complex is necessary. The chemical reducing agent serves to lower the oxidation state of the commercially obtained radioisotope, and a transchelator functions to maintain that lowered oxidation state prior to complexation with the linker molecule.

The commercially available form of $^{99m}$Tc is pertechnetate, TcO$_4^-$, in which the technetium is in the +7 oxidation state, typically denoted Tc(VII). Operationally, the technetium is reduced to Tc(V), Tc(IV), Tc(III), or Tc(I), by the use of stannous dichloride, Sn(II)Cl$_2$ [Pinkerton, T. C. et al., 1985, J. Chem. Ed. 62:965], by the use of stannous tartrate [Rhodes, B. A. et al., In: Tumor Imaging, Burchfield and Rhodes (Eds.), Masson, N.Y. 1983, p. 111], or by other inorganic chemical reducing agents, e.g., dithionite, borohydride, or ferrous ion in aqueous or aqueous-organic solutions at about pH 4 to about pH 7, or by other organic reducing agents [Thakur, M. L. et al., 1991, Int. J. Radiat. Appl. Instrum. Part B, 18:227–233]. The reducing agent, preferably stannous ion, should be added in excess to ensure reduction of the total amount of pertechnetate present. Reduction is normally effected under an inert gas atmosphere, e.g., nitrogen or argon, at about room temperature.

In the case of directly reduced biological molecules (see below), if excess stannous ions are not present, the biological molecule/technetium complex begins to oxidize, releasing Tc as pertechnetate ions [Burchfield and Rhodes, supra, at p. 113]. Furthermore, stabilizers for the stannous ion are advantageously present in the solution. It is known that ascorbate can improve specific loading of a chelator with reduced pertechnetate and minimize formation of TcO$_2$, when the reducing agent is stannous ion. Other polycarboxylic acids, e.g., tartrate, citrate, phthalate, iminodiacetate, ethylenediaminetetraacetic acid (EDTA), diethylenetriaminepentaacetic acid (DTPA), and the like can also be used. Although polycarboxylic acids are mentioned, by way of illustration, any variety of anionic and/or hydroxylic oxygen-containing species could serve this function, e.g., salicylates, acetylacetonates, hydroxyacids, and the like.

While the precise role of such agents is not known, it appears that they chelate stannous ion and may prevent adventitious reactions and/or promote reduction by stabilization of stannic ions, and they may also chelate—and thereby stabilize—certain oxidation states of reduced pertechnetate, thereby serving as transchelating agents for the transfer of these technetium ions to presumably more stable chelation with one or more thiol groups and other nearby ligands on the protein [PCT/US90/05196, Hansen, H. et al.].

The chemical reduction of pertechnetate is typically carried out in the presence of a molecule which will chelate the reduced technetium, and thereby hold the reduced technetium in a lower oxidation state. Such molecule is termed a transchelator.

An example of a transchelator is tricine and its function as such is described in European Patent Application EP 0 569 132 A1. Tricine, one of Good's buffers, [Biochemistry, 1966, Vol. 5, No. 2:467–477], has been used in various applications as a buffer [Calbiochem Biochemical/Immunological 1992 Catalog, BMC Biochemicals 1994 Catalog, both use tricine as a buffer for Endoproteinase Lys-C, sequencing grade] as well as a stabilizer of liquid formulations of radiolabelled compounds [U.S. Pat. No. 4,390,517]. Another example of a transchelator is found in Schwartz, D. A. et al., 1991, Bioconjugate Chem. 2:333–336. Commercially available kits which will form a $^{99m}$Tc-glucoheptonate complex are Glucoscan® and Gluceptate® sodium glucoheptonate kits available from DuPont Merck Pharmaceutical Co. and from Mallinckrodt, Inc., respectively.

That a transchelator can serve as a lyoprotectant to the conjugate molecule has not been described. The prior art taught that compounds such as sugars, e.g., mannitol, sucrose, and trehalose; amino acids, e.g., glycine; sugar alcohols; sugar acids; synthetic polymers and other proteins, e.g., HSA, could be used for such a purpose.

Fillers or bulking agents have often been employed in formulated aqueous protein-containing solutions where the combined concentration of other ingredients failed to allow the development of a physically robust cake. Fillers have been distinguished from other additives and employed to contribute bulk and mass to the dry product. It is understood that fillers may crystallize but that they may serve equally well where they persist in an amorphous state.

A general understanding of the physical chemistry of freezing and freeze-drying recognized a basic dichotomy in freezing behavior, all in accordance with the nature of the dissolved substances (and, to some extent, the nature of the freezing treatment). It was seen that dissolved constituents might crystallize with cooling and contribute to a eutectic behavior, or they might fail to crystallize, concentrating very highly, thereby persisting in an amorphous state and contribute to a non-eutectic state.

The understanding of the respective roles of buffer, lyoprotectant, and filler has developed in concert with the general understanding of freezing and freeze-drying behavior. Buffers, to function as such, should not crystallize during freezing or freeze-drying unless the protein is so stable that it is unaffected by the change in pH. Lyoprotectants should persist in amorphous states in order to embed protein and to prevent protein-protein interactions and other undesirable reactions. Fillers may crystallize or they may not providing that they contribute to the physical structure of the cake.

A pharmaceutical or diagnostic protein solution could be formulated with a buffer, a lyoprotectant, and a filler and the three distinct ingredients might be required. One might, for example, employ a TRIS/TRIS-HCl mixture to buffer, sucrose to lyoprotect, and mannitol to contribute cake mass. One might, on the other hand, employ a Na citrate/citric acid buffer solution to buffer, lyoprotect, and contribute cake mass. The same could be said of human serum albumin (HSA)—it is known to buffer, to protect many other proteins, and contribute mass, Na citrate buffers and HSA have each been used to fulfill these three separate needs.

Certain molecules that interact with specific targets or desired sites can be used as highly specific vehicles for the delivery of drugs or radioisotopes to target organs, tumors or thrombi in vivo. As one illustrative example, there are methods for the direct labeling of antibodies with radioisotopes, as described by Huang et al., 1980, J. Nucl. Med. 21:783 and by Rhodes, B. A. et al., In: Tumor Imaging, Burchield and Rhodes (Eds.), Masson, N.Y. (1983), p. 111. In these methods, disulfide linkages intrinsic to the antibodies are chemically reduced to generate free thiol groups, which are capable of binding radiometals such as technetium. There are two major disadvantages to the direct chemical reduction approach: (1) not all the proteins or peptides which are desirable as delivery vehicles contain readily reducible disulfide linkages and (2) chemical reduction can alter the biological activity of the reduced protein/peptide relative to the initial, unreduced protein/peptide.

Binding of the radioisotope to a linker molecule, which in turn is bound to the targeting molecule can overcome these disadvantages. The targeting molecule may be an antibody, or an antibody which has been chemically modified to facilitate binding to a linker molecule.

In the specific case of antibodies, which are glycoproteins, the linker molecule, as an example and not by way of limitation, may be attached to the carbohydrate moiety of the antibody. This may be done by first oxidizing the carbohydrate moiety to an aldehyde function. An example of addition of a linker to oxidized antibodies is provided in U.S. Pat. No. 4,741,900, incorporated herein by reference.

Various linker molecules have been proposed. The linker molecule performs two functions: (1) a given linker molecule contains functional groups which are reactive with functional groups on a given biological molecule (the targeting molecule) and (2) a given linker molecule contains functional groups which can hold a given radioisotope.

Of (1), there are linker molecules which are reactive with functional groups on proteins, especially antibodies or antibody fragments, peptides, nucleic acids or steroids. The specific functional groups of the biological molecule can include, but are not limited to, (a) oxidized carbohydrate moieties (in which case the functional group of the linker may be a primary amine, hydroxyl amine, hydrazide, thiohydrazide, phenylhydrazine, semicarbazide or thiosemicarbazide), (b) sulfhydryl (in which case the functional group of the linker may be pyridyl disulfide, haloacetate/haloacetamide or maleimide), (c) amino (in which case the functional group of the linker may be isothiocyanate, haloacetate/haloacetamide, carboxylic acid, ester or succinate) or (d) carboxylic (in which case the functional group of the linker may be an amine, hydrazide, or semicarbazide).

Of (2), the linker molecule can have functionality to hold the radioisotope to the linker molecule. In the case of a radiometal, such as $^{99m}$Tc, $^{186}$Re, or $^{188}$Re, appropriately spaced C=O, C=S, or other functionality may be appropriate to hold the radioisotope to the linker molecule.

A number of bifunctional chelating agents have been reported in the scientific literature. Tolman et al. [U.S. Pat. No. 4,732,864] have described the use of the cysteine rich, metal binding protein metallothonein and metallothionein fragments conjugated to targeting molecules. However, this method suffers from the fact that metallothonein is itself a large molecule and it may be difficult to purify and characterize such conjugates.

Schwartz et al. [PCT WO 94/10149; Schwartz, D. A. et al., 1991, Bioconjugate Chem. 2:333–336] describe a series of bifunctional technetium chelators based on pyridyl hydrazines.

Fritzberg et al. [EP 0188256; Fritzberg et al., 1988, Proc. Natl. Acad. Sci. U.S.A. 85:4025] have described several examples of bifunctional dithiolate diamide technetium chelators. However, such methods for chelation of technetium are cumbersome since the compounds must be pre-chelated to technetium and then conjugated to antibodies. Also such compounds require a free thiol group for technetium chelation.

Yokoyama et al. [U.S. Pat. No. 4,287,362; Arano et al., 1986, Int. J. Nucl. Med. Biol. 12:425; Yokoyama et al., 1987, J. Nucl. Med. 28:1027] describe bifunctional chelators based on thiocarbazone derivatives of 1,2 dicarbonyl compounds. These compounds have a thiocarbonyl moiety as the technetium chelating group.

EP 0 569 132 A1 discloses the use of tricine as a transchelator in a two component kit for the radiolabeling of conjugate molecules, specifically those containing 2-hydraminopyridine derivatives. This procedure required two distinct steps: (1) the combination of a solution of $^{99m}$TcO$_4^-$ with a lyophilized mixture of tin dichloride dihydrate and the transchelator tricine such that the Tc is reduced and chelated by tricine and (2) the combination of the resultant chemically reduced technetium solution with a solution of conjugate molecule.

For ease of storage and for ease of use, it is desirable that the components of the kit be lyophilized, which is to say, freeze-dried. It is well known to those skilled in the art that lyophilized products require a bulking agent that forms a cake and is instantly soluble upon rehydration. Typical bulking agents include sugars (e.g., mannitol, sucrose, trehalose) or amino acids (glycine). Proteins usually require a lyoprotectant during lyophilization, such that the protein is instantly soluble, does not aggregate, and retains its pharmaceutical activity upon rehydration. The issues involved in stabilizing proteins during freeze-drying have been discussed [Carpenter, J. F. et al., 1991, Develop. Biol. Standard. 74:225–239; MacKenzie, A. P., 1977, Develop. Biol. Standard. 36:51–67.]

In summary, for the formation of radioconjugates, particularly those containing Tc or Re, the prior art teaches a multistep process: the radioisotope is first reduced to a lower oxidation state in the presence of a transchelator, which maintains the lowered oxidation state, and then the solution of reduced radioisotope is combined with a conjugate molecule to form a radioconjugate.

Citation or identification of any reference in the background of this application shall not be construed as an admission that such reference is available as prior art to the present invention.

There are several drawbacks with the teachings of the prior art. In multistep procedures, there is a complexity not involved in single-step procedures, such that there is a greater possibility of error. Additionally, multistep procedures take more time and may use more reagents, thus are more expensive. Further, in the compositions of the prior art there are problems associated with low radiochemical purities, with unstable reducing agents and with unstable linker molecules. Therefore, it is desirable to be able to formulate a labeling kit such that the labeling process requires only one step and radiolabeling occurs quickly, efficiently, and such that high radiochemical purities are achieved.

3. SUMMARY OF THE INVENTION

The present invention is based, in part, on the surprising discovery that a chemical reducing agent, a transchelator, and a conjugate molecule can be lyophilized together to yield synergistic benefits in comparison to the prior art. The inventors observed that the conjugate molecule can stabilize the chemical reducing agent. The present inventors also unexpectedly observed that transchelators, such as tricine, are excellent lyoprotectant and bulking agents.

It is an object of the present invention to provide a novel lyoprotectant and bulking agent for the lyophilization of macromolecules, particularly proteins and proteinaceous materials.

Another object is to provide an instant kit formulation as well as an improved method for preparing radioconjugates.

Another object is to provide a novel reducing agent/transchelator/conjugate molecule formulation that overcomes the disadvantages of the prior art with respect to the slow kinetics of radiolabeling the conjugate molecule. In this embodiment of the invention, by reducing the two step process of radiolabeling a conjugate molecule to only one step wherein the conjugate molecule, the transchelator, and the reducing agent are all in one pot and lyophilized as a mixture and wherein a solution of a radioisotope, such as $^{99m}$Tc, is subsequently added to the lyophilized material, one obtains fast radiolabeling kinetics, for example, typically >95% Tc incorporated in less than about 15 minutes. According to this new formulation, high specific activity, >50 mCi/mg conjugate, and high radiochemical purity, >90%, are obtained such that post-radiolabeling purification becomes unnecessary.

Yet another object of the present invention is to stabilize the conjugate so as to prevent aggregation and articulate formation during lyophilization, such that there is no need to filter the composition before in vivo administration.

Many other advantages are realized over the prior art with the present invention, for example, using the transchelator as the lyoprotectant saves the cost of evaluating and using any other lyoprotectants. Additionally, the conjugate and reducing agent are combined earlier in the formulation of the present invention than in the prior art, and surprisingly, it was found that the conjugate actually helps to protect the reducing agent from oxidation, i.e., stabilizes the reducing agent.

As used in the present application, the term "macromolecule" encompasses proteinaceous materials, including peptide, polypeptide, protein, glycoprotein and proteoglycan substances.

As used in the present application, the term "targeting molecule" encompasses macromolecules which have the ability to distribute specifically to a cellular, tissue or organ site in vivo or in vitro, i.e., a target site.

Attachment of a linker molecule to a targeting molecule forms a conjugate. Chelation of a radiometal ion to a conjugate forms a "radioconjugate". Thus, the conjugates are useful to prepare radioconjugates, i.e., having attached a radioactive metal ion for use as in vivo therapeutics as well as in vivo and in vitro diagnostics. Specifically, the radioconjugates are used for detection or delivery of radiolabelled metal ions for imaging of specific tissues, for therapy at specific tissues or organ sites and immunological assays as described, for example, by U.S. Pat. No. 4,741,900.

Ideally, the linker and targeting molecule are combined prior to the introduction of a radiometal to form a conjugate molecule. In the present lyophilized formulation of a conjugate molecule the combination of the reducing agent and conjugate is found to stabilize the reducing agent with respect to oxidation by residual air (OXIDATION INHIBITION), and the transchelator is found to serve both as a lyoprotectant to the conjugate during the lyophilization process (LYOPROTECTION), and as a bulking agent.

The present invention provides compositions and methods for lyoprotecting a macromolecule comprising mixing a compound having the formula:

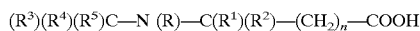

where R is hydrogen, hydroxy, alkyl, hydroxyalkyl, or alkylcarboxy, or R and $R^1$ together may form a mono-, di-, tri-, or tetra-methylene radical, or R and $R^2$ together may form a mono-, di-, tri-, or tetra-methylene radical, and $R^1$ and $R^2$ may be the same or different and are selected from hydrogen, hydroxy, alkyl, hydroxyalkyl, carboxy, alkylcarboxy, alkylamine, alkylthiol and aryl or $R^1$ and $R^2$ together may form a tetra- or penta-methylene radical, and $R^3$ and $R^4$ and $R^5$ may be the same or different and are selected from hydrogen, hydroxy, alkyl, hydroxyalkyl, carboxy and alkylcarboxy, provided that at least one of $R^3$, $R^4$ and $R^5$ is hydroxyalkyl, and n is equal to 0, 1 or 2 with a macromolecule in an aqueous solution wherein the resultant mixture is lyophilized.

Preferred alkyl and substituted alkyl groups for R are alkyl of 1 to 3 carbon atoms. Preferably, when $R^1$ and $R^2$ are alkyl or substituted alkyl, they are 1 to 4 carbon atoms. Preferred aryl groups are phenyl and benzyl. Preferably, when $R^3$ and $R^4$ and $R^5$ are alkyl or substituted alkyl groups they are 1 to 3 carbon atoms.

Preferably, at least one of R, $R^1$ and $R^2$ is hydrogen and at least one of $R^3{}_1$, $R^4$ and $R^5$ is hydroxymethyl. In a particularly preferred embodiment, the lyoprotectant is N-[tris(hydroxymethyl)methyl]glycine, also known as tricine. Other desirable compounds are those in which R, $R^1$ and $R^2$ are all hydrogen, $R^3$ is hydrogen, methyl or ethyl, and $R^4$ and $R^5$ are hydroxymethyl or 2-hydroxyethyl; R, $R^1$ and $R^2$ are all hydrogen, $R^3$ and $R^4$ are hydrogen or methyl, and $R^5$ is hydroxymethyl or 2-hydroxyethyl. Also desirable are compounds in which R and $R^1$ are both hydrogen, $R^2$ is methyl hydroxy, hydroxymethyl, carboxy, carboxymethyl, 2-carboxyethyl, phenyl, benzyl, 1-hydroxyethyl or mercaptomethyl, and $R^3$, $R^4$ and $R^5$ are all hydroxymethyl; R is hydrogen, $R^1$ and $R^2$ are both methyl, and $R^3$, $R^4$ and $R^5$ are all hydroxymethyl; R is hydroxy, hydroxymethyl, or carboxymethyl, $R^1$ and $R^2$ are both hydrogen, and $R^3$, $R^4$ and $R^5$ are all hydroxymethyl.

Further, the present invention provides a lyophilized formulation which is suitable for radiolabeling a conjugate molecule comprising: a compound having the formula:

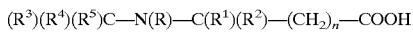

where R is hydrogen, hydroxy, alkyl, hydroxyalkyl, or alkylcarboxy, or R and $R^1$ together may form a mono-, di-, tri-, or tetra-methylene radical, or R and $R^2$ together may form a mono-, di-, tri-, or tetra-methylene radical, and $R^1$ and $R^2$ may be the same or different and are selected from hydrogen, hydroxy, alkyl, hydroxyalkyl, carboxy, alkylcarboxy, alkylamine, alkylthiol and aryl or $R^1$ and $R^2$ together may form a tetra- or penta-methylene radical, and $R^3$ and $R^4$ and $R^5$ may be the same or different and are selected from hydrogen, hydroxy, alkyl, hydroxyalkyl, carboxy and alkylcarboxy, provided that at least one of $R^3$, $R^4$ and $R^5$ is hydroxyalkyl, and n is equal to 0, 1 or 2, a chemical reducing agent, and a conjugate molecule, wherein the conjugate molecule comprises a targeting molecule covalently attached to a linker. In a preferred embodiment, the lyophilized formulation is suitable for mixing with a solution of radioactive Tc or Re, thus, forming a radioconjugate.

Preferred alkyl and substituted alkyl groups for R are alkyl of 1 to 3 carbon atoms. Preferably, when $R^1$ and $R^2$ are alkyl or substituted alkyl, they are 1 to 4 carbon atoms. Preferred aryl groups are phenyl and benzyl. Preferably, when $R^3$ and $R^4$ and $R^5$ are alkyl or substituted alkyl groups they are 1 to 3 carbon atoms.

Preferably, at least one of R, $R^1$ and $R^2$ is hydrogen and at least one of $R^3$, $R^4$ and $R^5$ is hydroxymethyl. In a particularly preferred embodiment, the compound is N-[tris(hydroxymethyl)methyl]glycine, also known as tricine.

Other desirable compounds are those in which R, $R^1$ and $R^2$ are all hydrogen, $R^3$ is hydrogen, methyl or ethyl, and $R^4$ and $R^5$ are hydroxymethyl or 2-hydroxyethyl; R, $R^1$ and $R^2$ are all hydrogen, $R^3$ and $R^4$ are hydrogen or methyl, and $R^5$ is hydroxymethyl or 2-hydroxyethyl. Also desirable are compounds in which R and $R^1$ are both hydrogen, $R^2$ is methyl hydroxy, hydroxymethyl, carboxy, carboxymethyl, 2-carboxyethyl, phenyl, benzyl, 1-hydroxyethyl or mercaptomethyl, and $R^3$, $R^4$ and $R^5$ are all hydroxymethyl; R is hydrogen, $R^1$ and $R^2$ are both methyl, and $R^3$, $R^4$ and $R^5$ are all hydroxymethyl; R is hydroxy, hydroxymethyl, or carboxymethyl, $R^1$ and $R^2$ are both hydrogen, and $R^3$, $R^4$ and $R^5$ are all hydroxymethyl.

The present invention additionally provides an instant kit comprising a lyophilized mixture of the above described formulation components. The kits may further comprise inert ingredients and other kit components such as vials, caps and the like, known to those skilled in the art.

The present invention also relates to a process for forming a kit which is suitable for combining with a radioactive Tc or Re solution, which comprises lyophilizing a mixture of a chemical reducing agent, a compound having the formula:

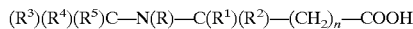

$$(R^3)(R^4)(R^5)C-N(R)-C(R^1)(R^2)-(CH_2)_n-COOH$$

where R is hydrogen, hydroxy, alkyl, hydroxyalkyl, or alkylcarboxy, or R and $R^1$ together may form a mono-, di-, tri-, or tetra-methylene radical, or R and $R^2$ together may form a mono-, di-, tri-, or tetra-methylene radical, and $R^1$ and $R^2$ may be the same or different and are selected from hydrogen, hydroxy, alkyl, hydroxyalkyl, carboxy, alkylcarboxy, alkylamine, alkylthiol and aryl or $R^1$ and $R^2$ together may form a tetra- or penta-methylene radical, and $R^3$ and $R^4$ and $R^5$ may be the same or different and are selected from hydrogen, hydroxy, alkyl, hydroxyalkyl, carboxy and alkylcarboxy, provided that at least one of $R^3$, $R^4$ and $R^5$ is hydroxyalkyl, and n is equal to 0, 1 or 2, and a conjugate molecule which comprises a targeting molecule covalently attached to a linker molecule capable of chelating radioactive Tc or Re.

Preferred alkyl and substituted alkyl groups for R are alkyl of 1 to 3 carbon atoms. Preferably, when $R^1$ and $R^2$ are alkyl or substituted alkyl, they are 1 to 4 carbon atoms. Preferred aryl groups are phenyl and benzyl. Preferably, when $R^3$ and $R^4$ and $R^5$ are alkyl or substituted alkyl groups they are 1 to 3 carbon atoms.

Preferably, at least one of R, $R^1$ and $R^2$ is hydrogen and at least one of $R^3$, $R^4$ and $R^5$ is hydroxymethyl. In a particularly preferred embodiment, the compound is N-[tris (hydroxymethyl)methyl]glycine, also known as tricine. Other desirable compounds are those in which R, $R^1$ and $R^2$ are all hydrogen, $R^3$ is hydrogen, methyl or ethyl, and $R^4$ and $R^5$ are hydroxymethyl or 2-hydroxyethyl; R, $R^1$ and $R^2$ are all hydrogen, $R^3$ and $R^4$ are hydrogen or methyl, and $R^5$ is hydroxymethyl or 2-hydroxyethyl. Also desirable are compounds in which R and $R^1$ are both hydrogen, $R^2$ is methyl hydroxy, hydroxymethyl, carboxy, carboxymethyl, 2-carboxyethyl, phenyl, benzyl, 1-hydroxyethyl or mercaptomethyl, and $R^3$, $R^4$ and $R^5$ are all hydroxymethyl; R is hydrogen, $R^1$ and $R^2$ are both methyl, and $R^3$, $R^4$ and $R^5$ are all hydroxymethyl; R is hydroxy, hydroxymethyl, or carboxymethyl, $R^1$ and $R^2$ are both hydrogen, and $R^3$, $R^4$ and $R^5$ are all hydroxymethyl.

The present invention may be more fully understood by reference to the following detailed description, examples of specific embodiments and appended figures which are offered for purposes of illustration only and not by way of limitation.

4. BRIEF DESCRIPTION OF THE FIGURES

FIG. 1. A representative lyophilization cycle used to lyophilize a one-pot formulation mixture of tin, tricine, and conjugate.

Figure 2:
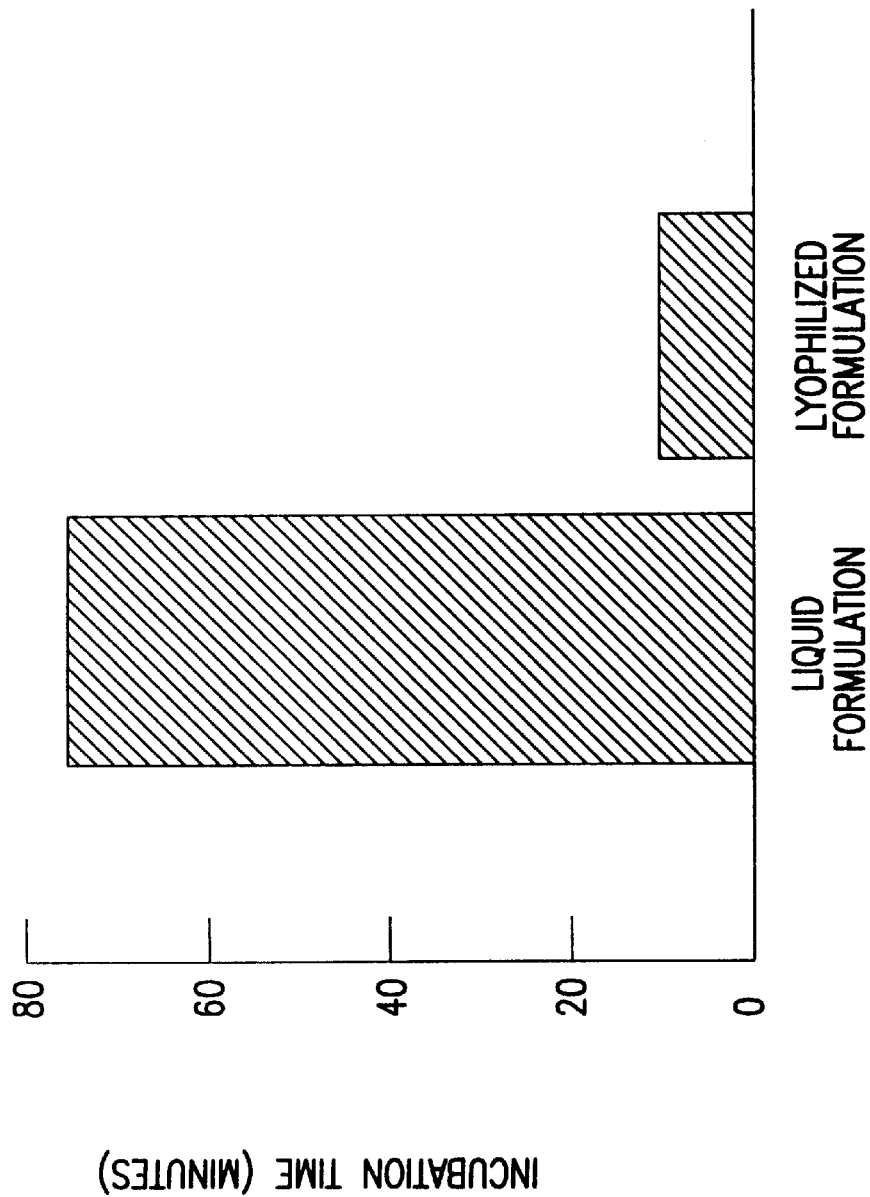

FIG. 2. Comparison of incubation times to achieve greater than 95% incorporation of $^{99m}$Tc by a radioimmunoconjugate prepared using the lyophilized kit of the present invention (LYOPHILIZED FORMULATION) and using a fresh two pot liquid formulation (LIQUID FORMULATION).

Figure 3:
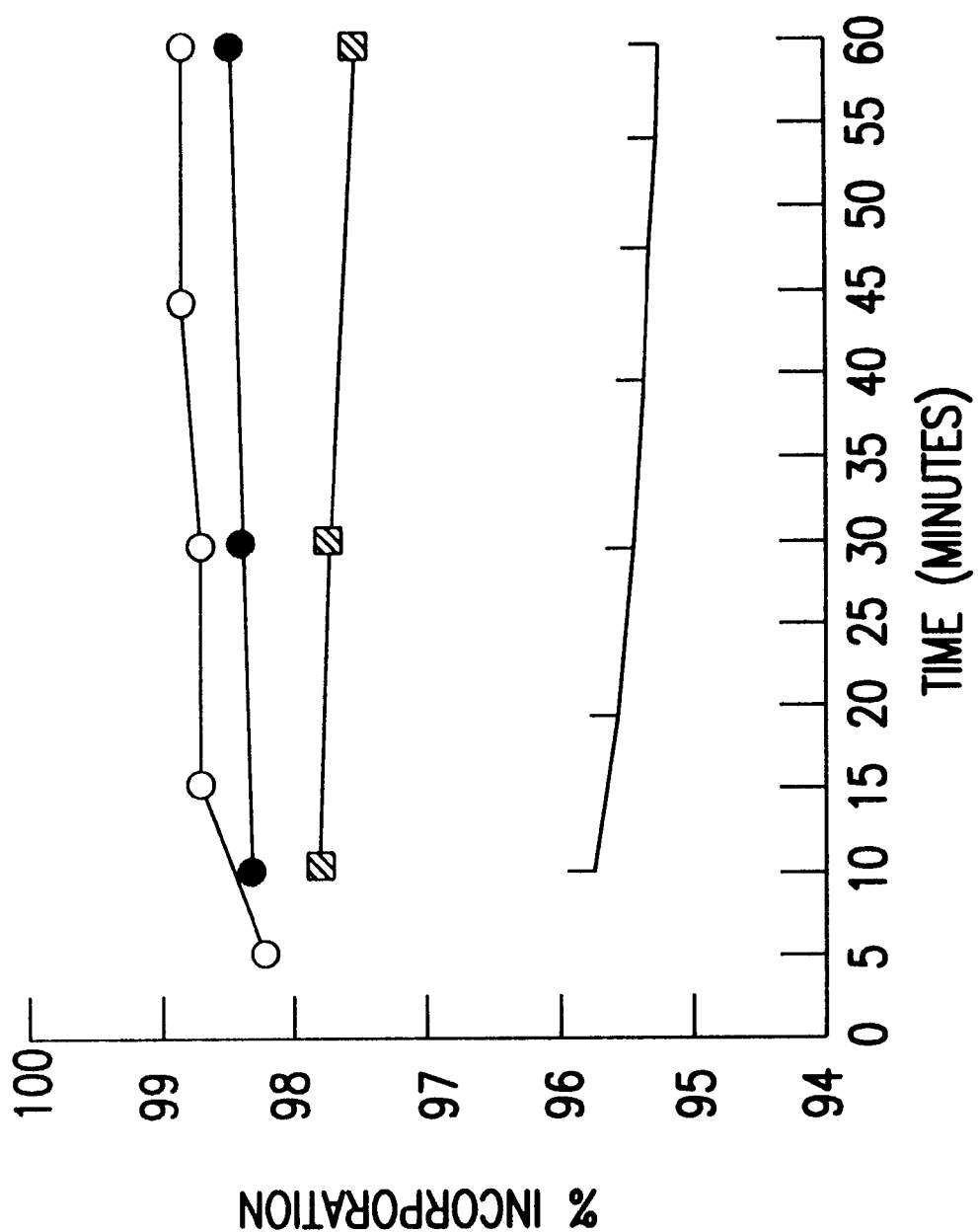

FIG. 3. Labeling kinetics of the one-pot instant kit formulation of the present invention. -O-, 50 mCi/mg-Exp.1; -✳-, 50mCi/mg-Exp2; -■- 100mCi/mg; -∇- 200 mCi/mg.

Figure 4:
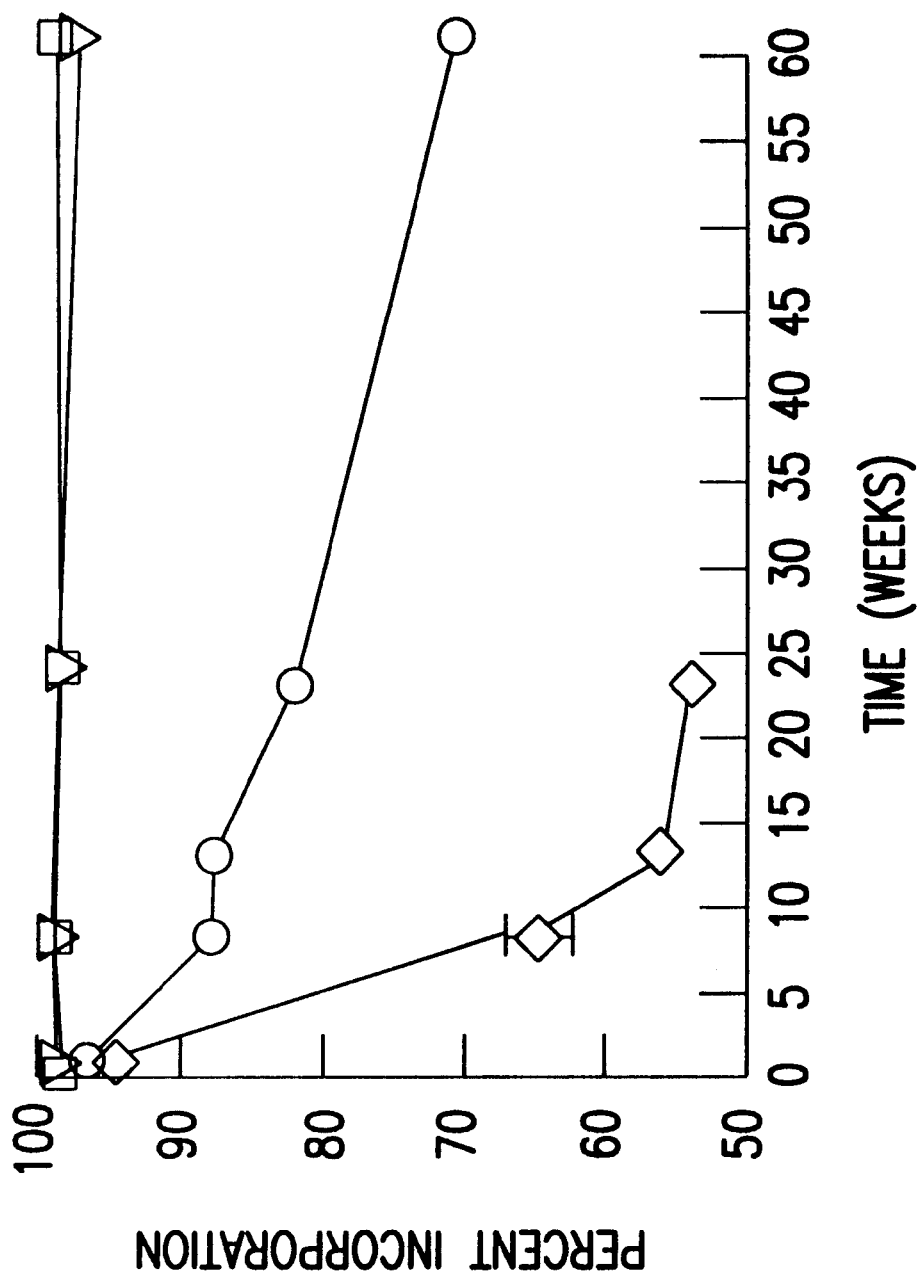

FIG. 4. A graph comparing $^{99m}$Tc incorporation by the lyophilized kit formulation of the present invention stored at 2–8° C. or 25° C. and by a fresh two pot liquid formulation stored at 2–8° C. or 25° C. over a time period of 61 weeks. -O-, Liquid formulation stored at 2–8° C.; -□-, Liquid formulation stored at 25° C.; -◇-, Lyophilized kit stored at 2–8° C.; -△-, lyophilized kit stored at 25° C. (Lyophilized 2–8° C. line overlays that of lyophilized 25° C. line).

Figure 5A:
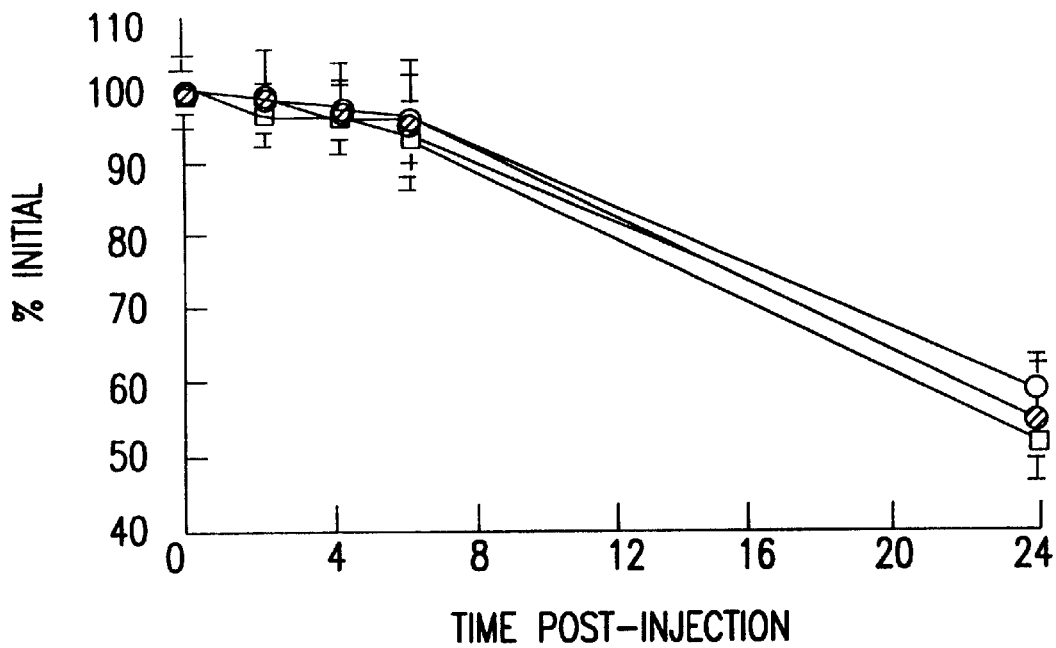
Figure 5B:
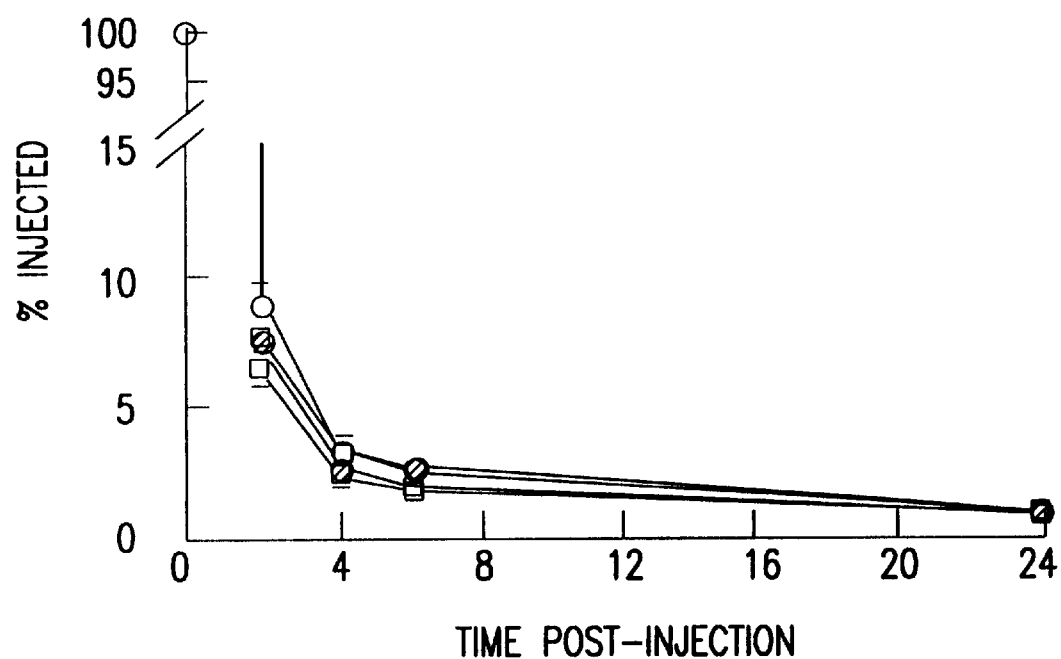

FIGS. 5a–b. FIG. 5a: A graph comparing Whole Body Clearance rates of CYT-402 radioconjugate produced by the lyophilized kit of the present invention and of a fresh two pot method liquid formulation of the same radioconjugate, but not lyophilized, in normal and tumor-bearing animals. FIG. 5b: A graph comparing Blood Clearance rates of CYT-402 radioconjugate produced by the lyophilized kit of the present invention and of a fresh two pot method liquid formulation of the same radioconjugate, but not lyophilized, in normal and tumor-bearing animals. In both FIGS. 5a and 5b: -●-, Lyophilized kit in tumor-bearing animals; -O-, Liquid formulation in tumor-bearing animals; -■-, Lyophilized kit in normal animals; -◇-, Liquid formulation in normal animals.

Figure 6A:
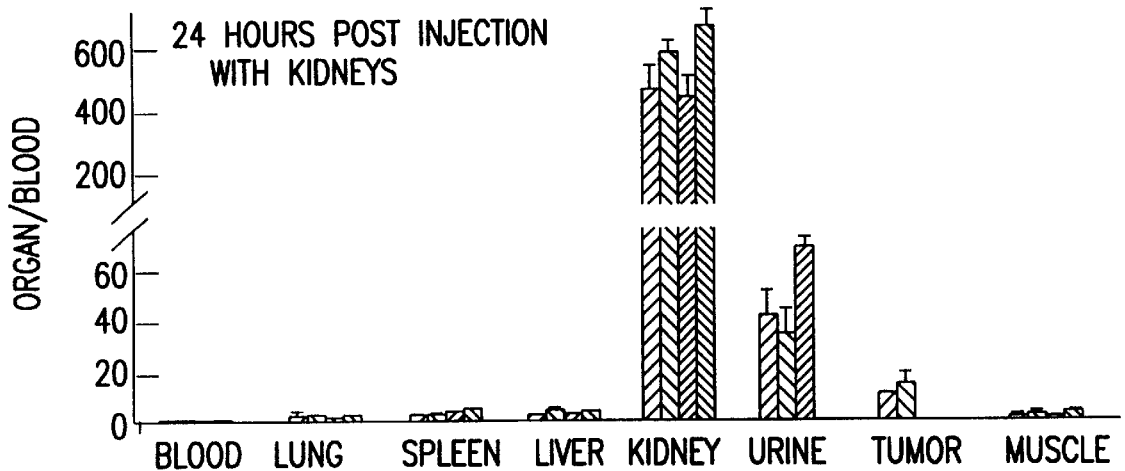
Figure 6B:
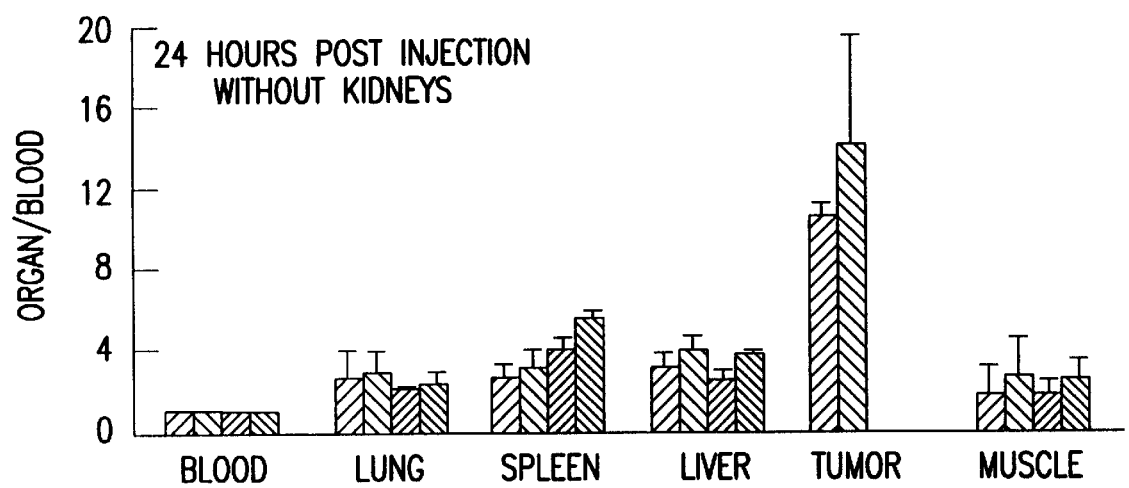
Figure 6C:
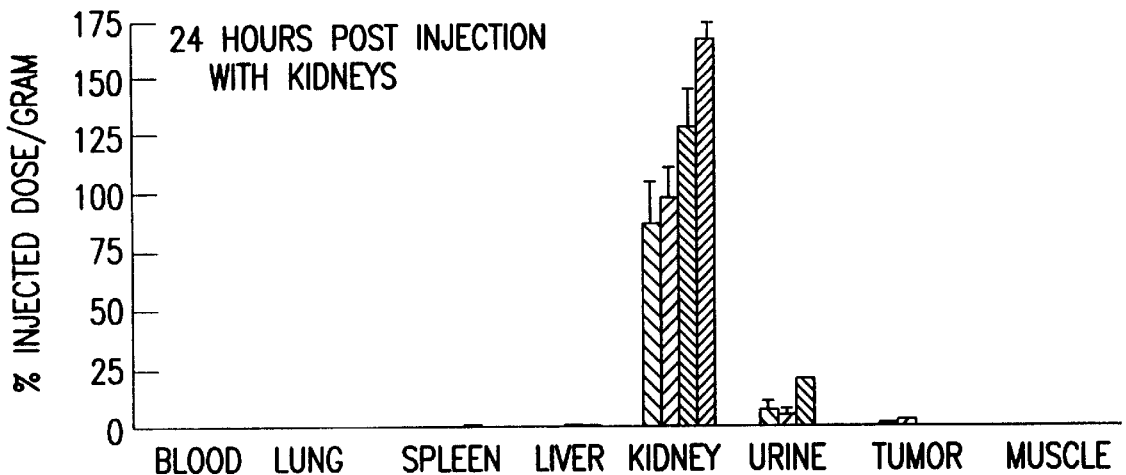
Figure 6D:
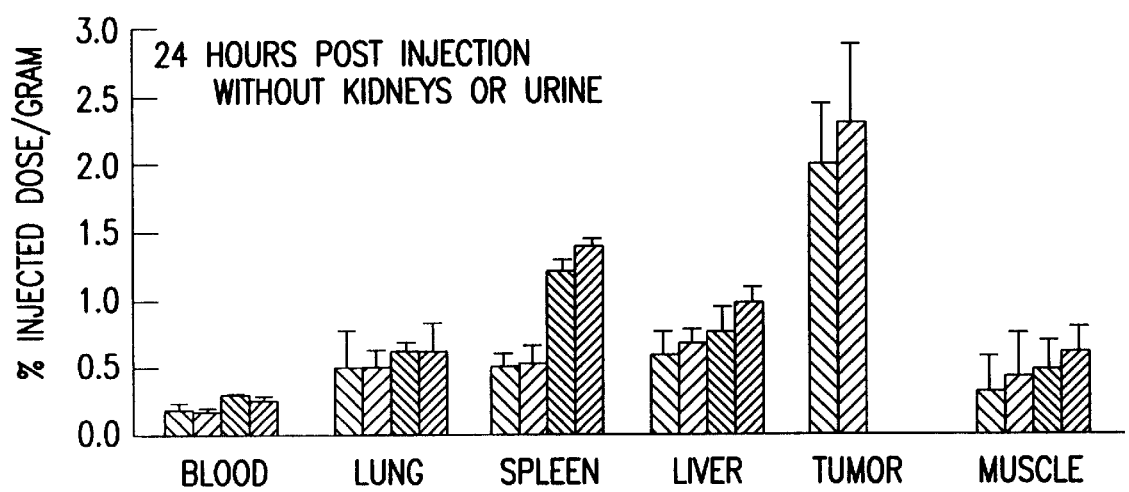

FIGS. 6a–d. The biodistribution of $^{99m}$Tc labeled CYT-402 radioconjugate prepared using the lyophilized kit of the present invention and of a fresh two pot method liquid formulation of the same immunoconjugate, but not lyophilized. FIG. 6a. Organ/blood ratio including kidney and urine data. FIG. 6b. Organ/blood ratio without kidney and urine data. FIG. 6c. Percent injected dose/gm of organ tested including kidney and urine data. FIG. 6d. Percent dose/gm of organ tested without kidney and urine data. In FIGS. 6a–d: ▨ Lyophilized kit in mice bearing tumors, ▧ liquid formulation in mice bearing tumors, ▭ lyophilized kit in normal mice, ▦ liquid formulation in normal mice.

Figure 7A:
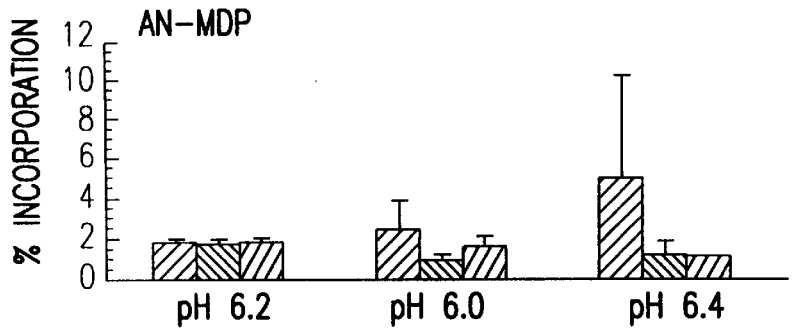
Figure 7B:
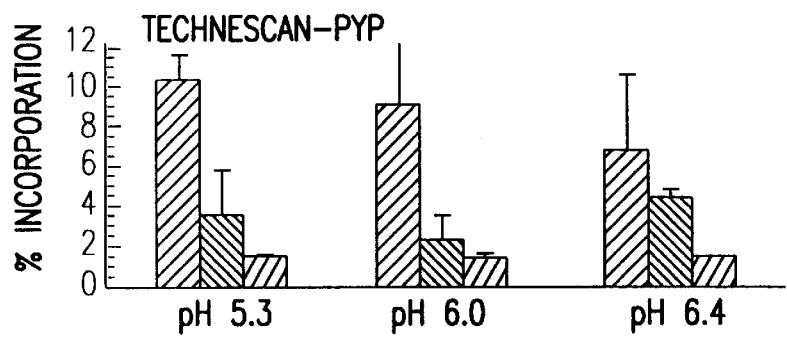
Figure 7C:
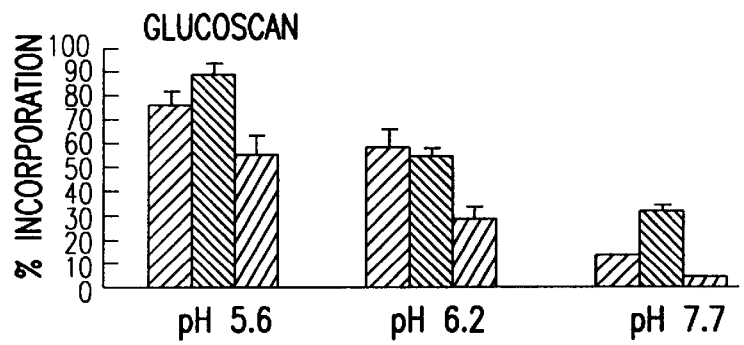
Figure 7D:
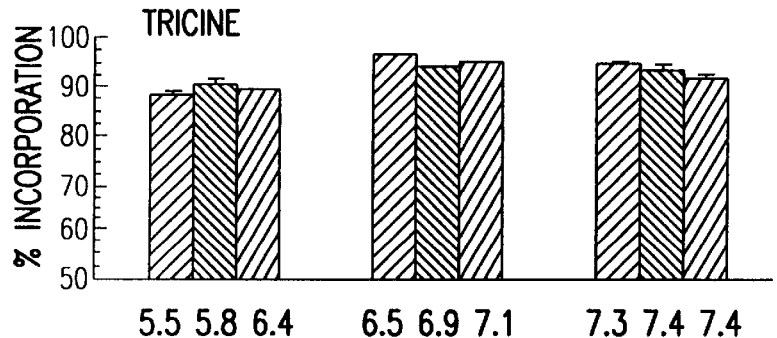

FIGS. 7a–d. Effect of Transchelator on $^{99m}$Tc labeling of immunoconjugate CYT-421. FIG. 7a: Transchelator was an AN-MDP® kit; FIG. 7b: Transchelator was a TechneScan®-PYP® kit; FIG. 7c: Transchelator was a Glucoscan® kit; FIG. 7d: Transchelator was tricine, according to the present invention. See text for details. In FIGS. 7a–d: ▨ 10 mCi/mg, ▬ 25 mCi/mg, ▧ 50 mCi/mg.

Figure 8:
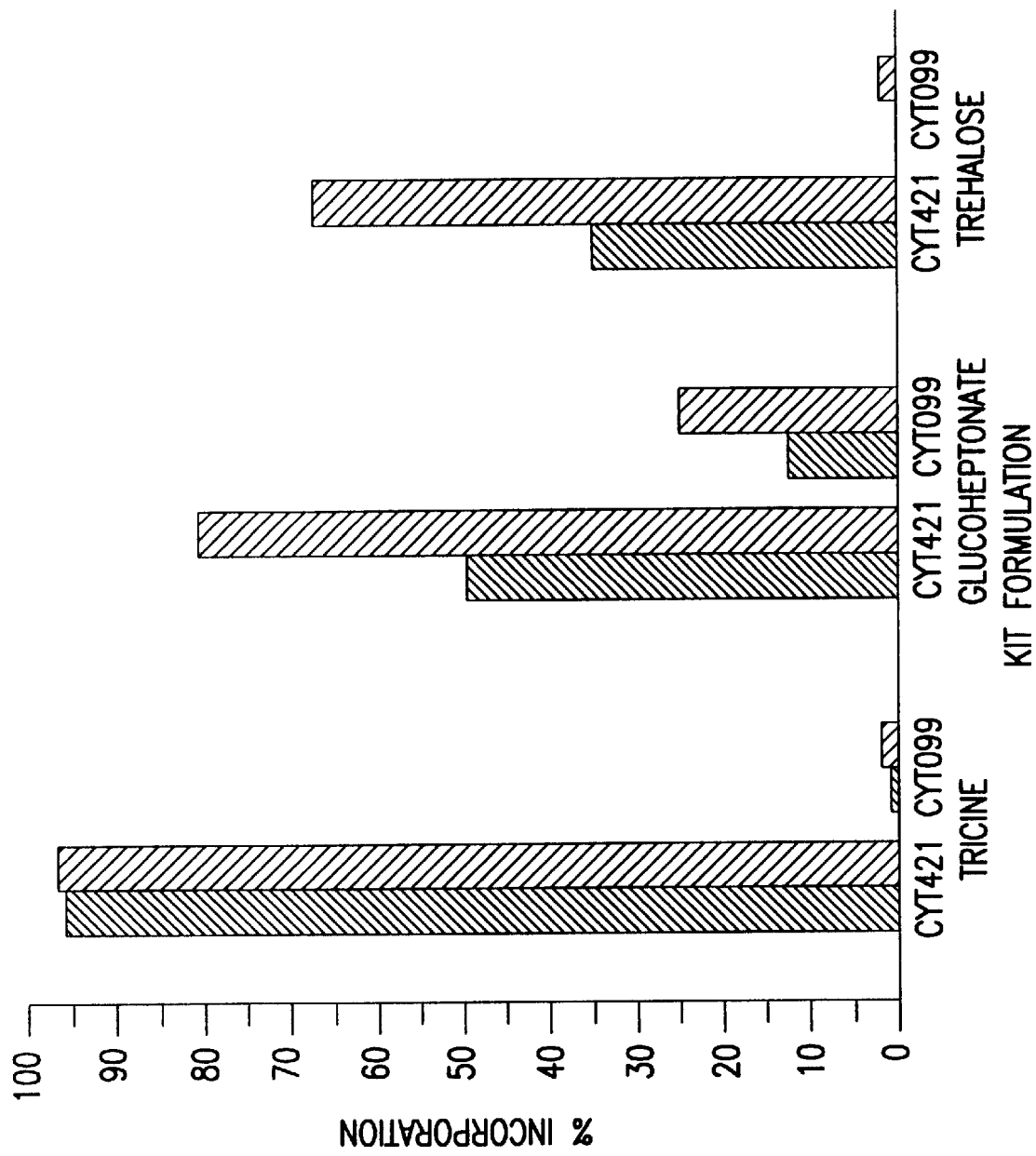

FIG. 8. Effect of Transchelator on $^{99m}$Tc labeling of immunoconjugate CYT-421 and monoclonal antibody CYT-099 for two incubation time periods. ▧ 20 minutes, 1 hour.

Figure 9A:
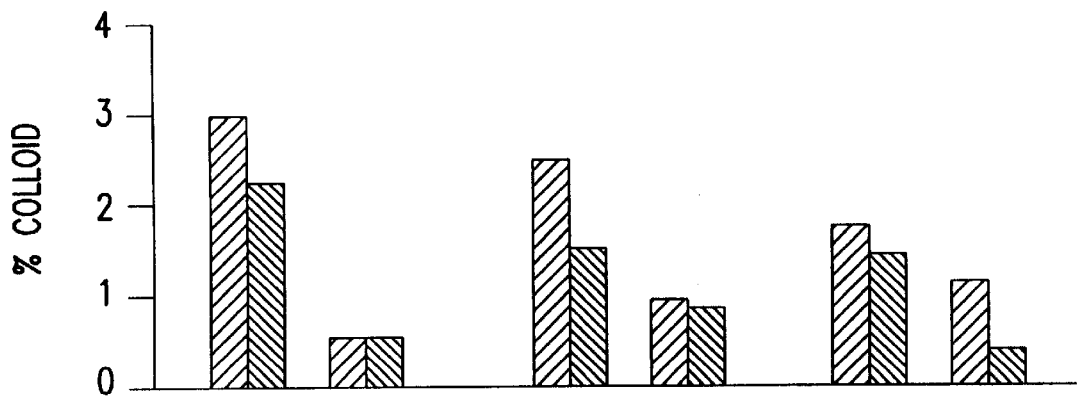
Figure 9B:
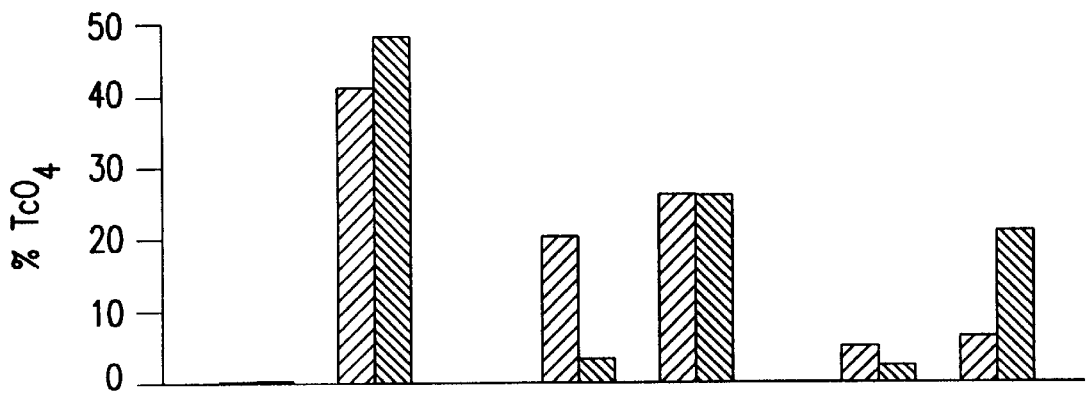
Figure 9C:
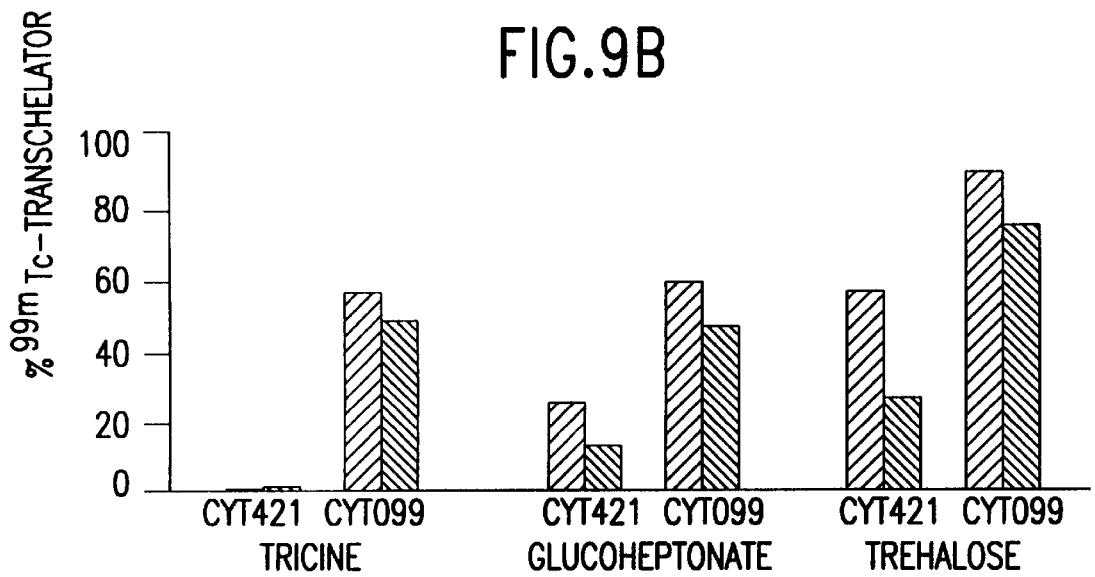

FIGS. 9a–c. Effect on Transchelator on $^{99m}$Tc labeling of immunoconjugate CYT-421 and monoclonal antibody CYT-099 for two incubation time periods. FIG. 9a. % colloid. FIGS. 9b. % $^{99m}$TcO$_4^-$. FIG. 9c. % $^{99m}$Tc-transchelator complex. In FIGS. 9a–c: ▨ 20 minutes, ▧ 1 hour.

Figure 10:
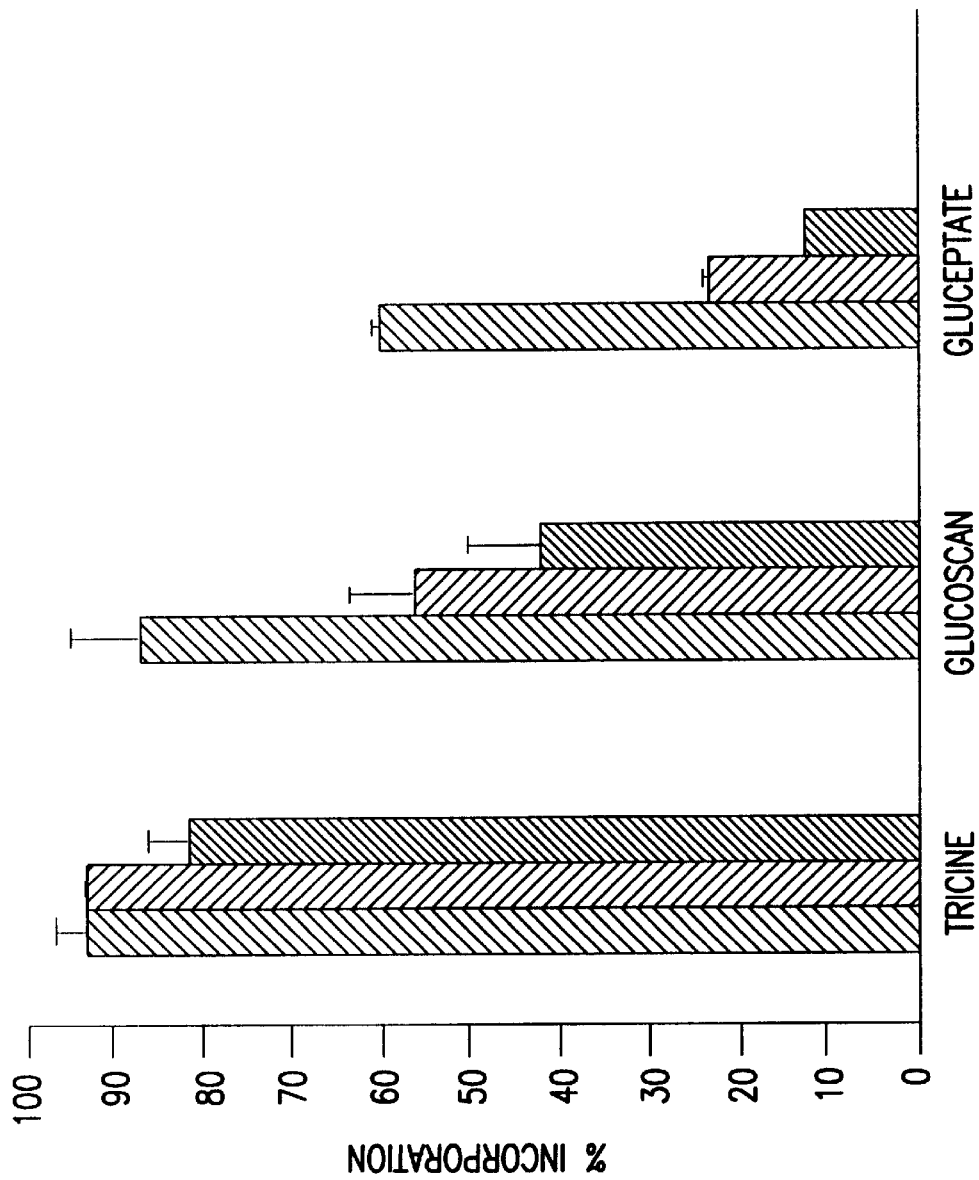

FIG. 10. Effect of Transchelator on $^{99m}$Tc labeling of immunoconjugate CYT-422. 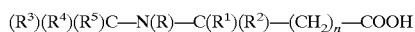 10 mCi/mg, 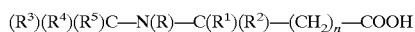 25 mCi/mg, 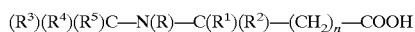 50 mCi/mg.

5. DETAILED DESCRIPTION OF THE INVENTION

5.1. Novel Lyoprotectants

According to one embodiment, the invention comprises a novel lyoprotectant/filler or bulking agent for macromolecules, which encompass proteinaceous materials, including peptide, polypeptide, protein, glycoprotein and proteoglycan substances. Lyophilized or freeze-dried products, such as proteins, require a bulking agent/lyoprotectant that forms a cake that is instantly soluble upon rehydration which protects the product from damage due to freezing and/or dehydration. Specifically, the purpose of the lyoprotectant is to insure that the lyophilized macromolecule does not aggregate upon rehydration and that the product substantially retains its biological/pharmaceutical activity. "Lyoprotectants" have been understood to function as such as a result of their tendencies to develop, and to persist in the form of glass-like concentrates (in which, for example, protein molecules are safely incorporated). Lyoprotection is lost if the lyoprotectant crystallizes.

This embodiment of the present invention is based on the discovery that a compound having the formula:

$$(R^3)(R^4)(R^5)C-N(R)-C(R^1)(R^2)-(CH_2)_n-COOH$$

where R is hydrogen, hydroxy, alkyl, hydroxyalkyl, or alkylcarboxy, or R and $R^1$ together may form a mono-, di-, tri-, or tetra-methylene radical, or R and $R^2$ together may form a mono-, di-, tri-, or tetra-methylene radical, and $R^1$ and $R^2$ may be the same or different and are selected from hydrogen, hydroxy, alkyl, hydroxyalkyl, carboxy, alkylcarboxy, alkylamine, alkylthiol and aryl or $R^1$ and $R^2$ together may form a tetra- or penta-methylene radical, and $R^3$ and $R^4$ and $R^5$ may be the same or different and are selected from hydrogen, hydroxy, alkyl, hydroxyalkyl, carboxy and alkylcarboxy, provided that at least one of $R^3$, $R^4$ and $R^5$ is hydroxyalkyl, and n is equal to 0, 1 or 2, is a very effective lyoprotectant and bulking agent for macromolecules or macromolecular compositions.

Preferred alkyl and substituted alkyl groups for R are alkyl of 1 to 3 carbon atoms. Preferably, when $R^1$ and $R^2$ are alkyl or substituted alkyl, they are 1 to 4 carbon atoms. Preferred aryl groups are phenyl and benzyl. Preferably, when $R^3$ and $R^4$ and $R^5$ are alkyl or substituted alkyl groups they are 1 to 3 carbon atoms.

Preferably, at least one of R, $R^1$ and $R^2$ is hydrogen and at least one of $R^3$, $R^4$ and $R^5$ is hydroxymethyl. Other desirable compounds are those in which R, $R^1$ and $R^2$ are all hydrogen, $R^3$ is hydrogen, methyl or ethyl, and $R^4$ and $R^5$ are hydroxymethyl or 2-hydroxyethyl; R, $R^1$ and $R^2$ are all hydrogen, $R^3$ and $R^4$ are hydrogen or methyl, and $R^5$ is hydroxymethyl or 2-hydroxyethyl. Also desirable are compounds in which R and $R^1$ are both hydrogen, $R^2$ is methyl hydroxy, hydroxymethyl, carboxy, carboxymethyl, 2-carboxyethyl, phenyl, benzyl, 1-hydroxyethyl or mercaptomethyl, and $R^3$, $R^4$ and $R^5$ are all hydroxymethyl; R is hydrogen, $R^1$ and $R^2$ are both methyl, and $R^3$, $R^4$ and $R^5$ are all hydroxymethyl; R is hydroxy, hydroxymethyl, or carboxymethyl, $R^1$ and $R^2$ are both hydrogen, and $R^3$, $R^4$ and $R^5$ are all hydroxymethyl.

In a preferred embodiment the compound is N-[tris (hydroxymethyl)methyl]glycine, also known as tricine. In this preferred embodiment tricine, is used at a pH value in which the buffering capacity of tricine is of no value. The range at which tricine is an effective buffer is about pH 7.15–9.15. The preferred pH for the specific embodiments of the invention is about pH 5. Further, tricine is also used in amounts of 10–200 mg/ml, which is typically more than those amounts used when tricine is used as a buffer.

Supporting the findings of this discovery are the results of thermal analyses and freezing microscopy studies, in which it was found that tricine is more difficult than mannitol to crystalize, see Section 6.1, infra. Differential thermal analysis (DTA) and Electrical Resistance (ER) measurements demonstrated the characteristic freezing/thawing behavior of an aqueous tricine solution. These studies revealed the development and persistence of a concentrated amorphous tricine phase in the presence of ice and the subsequent softening of that phase during warming. Correspondingly, they did not reveal any of the thermal behavior associated with the crystallization of a dissolved solute or of its subsequent eutectic melting. Eutectic behavior was very obviously absent. The $T_g{}'$, the temperature at which the glassy tricine concentrate softens abruptly was seen close to, and a little above –40° C. The behavior upon cooling of an aqueous tricine solution observed by cryomicroscopy techniques (see A. P. MacKenzie, 1975, In:Freeze Drying and Advanced Food Technology, Goldblith et al., (Eds.), Academic Press, NY) failed to reveal any crystallization of tricine. Concentrated amorphous aqueous tricine persisted as such at all temperatures to –20° C. By freeze-drying microscopy, an aqueous tricine solution was seen to proceed with retention at –50, –45 and –40° C. and with collapse at –35 and –30° C. All experiments point to a consistent freezing/thawing behavior of aqueous tricine solutions that make it a desirable cryoprotectant. An aqueous solution of tricine will crystallize only under extreme conditions and when the solution has been seeded with dry tricine. This observed crystallization proceeds very slowly, too slowly to allow crystallization during a normal freezing cycle during lyophilization (see for example Section 6.1).

Lyophilization processes are well known in the art and an appropriate lyophilization cycle could easily be designed based on the data presented in the Examples, see infra. For example, FIG. 1 shows an illustrative lyophilization cycle that results in an acceptable product. Preferably, however, the primary drying cycle would be about 6–20 hours, more preferably about 10–15 hours.

According to one embodiment, tricine at 10–200 mg/ml is used as a lyoprotectant for macromolecules. Preferably, it is used in a range of about 18–150 mg/ml and most preferably 18–144 mg/ml. One simply mixes tricine with the desired macromolecule in an aqueous solution that optionally contains a buffer and the resultant mixture is lyophilized. Using tricine as a lyoprotectant, entails using it in a range of about 80% to about 99+% of the mixture of active ingredients, more preferably about 90% to about 99%, most preferably about 95% to about 99%. In a preferred embodiment, the solution containing the macromolecule is typically formulated outside of tricine's effective biological buffering range (approximately pH 7.15–9.15), preferably about pH 5.

5.2. One Pot Lyophilized Formulation and Kit

Another embodiment of the present invention relates to novel compositions for the formation of a lyophilized formulation as well as an instant kit for the formation of a radiopharmaceutical. The radiopharmaceutical, which in a preferred embodiment is a radioconjugate, formed using the formulation or kit can be used for in vivo imaging or therapy. The lyophilized formulation or kit comprises a lyophilized mixture of the following components: a chemical reducing agent, a transchelator, and a conjugate of a linker and a targeting molecule. The kit may further comprise other kit components known to those skilled in the art.

Solely for ease of explanation, the description of this embodiment of the invention is divided into the following sections: i) Chemical reducing agent; ii) Transchelator; iii) Linker; iv) Targeting molecule; and v) One pot method for lyophilization.

5.2.1. Chemical Reducing Agent

The chemical reducing agent serves to reduce a radioisotope in an high oxidation state to a lower oxidation state, from which the radioisotope can be chelated by the transchelator and linker molecule. For use with Tc or Re, the reducing agent can be stannous ion ($Sn^{+2}$), ferrous ion ($Fe^{+2}$), or dithionite ion ($S_2O_4^{2-}$), also termed hydrosulfite. Most preferably, it is stannous ion formed from stannous chloride dihydrate. As a weight fraction of the weight of the active components of the kit, the stannous chloride dihydrate fraction preferably should be in the range 0.1% to 0.6%, most preferably in the range 0.1% to 0.2%. The active components of the kit do not take into account inert ingredients, vials, caps, packaging material and the like. The kits of the present invention advantageously permit lower than conventional amounts of reducing agent to be employed and provide a good stability profile for the reducing agent.

5.2.2. Transchelator

The transchelator serves to hold chemically reduced radioisotopes in a lower oxidation state prior to association with the linker molecule. According to the present invention, the transchelator is a compound of the formula:

where R is hydrogen, hydroxy, alkyl, hydroxyalkyl, or alkylcarboxy, or R and $R^1$ together may form a mono-, di-, tri-, or tetra-methylene radical, or R and $R^2$ together may form a mono-, di-, tri-, or tetra-methylene radical, and $R^1$ and $R^2$ may be the same or different and are selected from hydrogen, hydroxy, alkyl, hydroxyalkyl, carboxy, alkylcarboxy, alkylamine, alkylthiol and aryl or $R^1$ and $R^2$ together may form a tetra- or penta-methylene radical, and $R^3$ and $R^4$ and $R^5$ may be the same or different and are selected from hydrogen, hydroxy, alkyl, hydroxyalkyl, carboxy and alkylcarboxy, provided that at least one of $R^3$, $R^4$ and $R^5$ is hydroxyalkyl, and n is equal to 0, 1 or 2.

Preferred alkyl and substituted alkyl groups for R are alkyl of 1 to 3 carbon atoms. Preferably, when $R^1$ and $R^2$ are alkyl or substituted alkyl, they are 1 to 4 carbon atoms. Preferred aryl groups are phenyl and benzyl. Preferably, when $R^3$ and $R^4$ and $R^5$ are alkyl or substituted alkyl groups they are 1 to 3 carbon atoms.

Preferably, at least one of R, $R^1$ and $R^2$ is hydrogen and at least one of $R^3$, $R^4$ and $R^5$ is hydroxymethyl. Other desirable compounds are those in which R, $R^1$ and $R^2$ are all hydrogen, $R^3$ is hydrogen, methyl or ethyl, and $R^4$ and $R^5$ are hydroxymethyl or 2-hydroxyethyl; R, $R^1$ and $R^2$ are all hydrogen, $R^3$ and $R^4$ are hydrogen or methyl, and $R^5$ is hydroxymethyl or 2-hydroxyethyl. Also desirable are compounds in which R and $R^1$ are both hydrogen, $R^2$ is methyl hydroxy, hydroxymethyl, carboxy, carboxymethyl, 2-carboxyethyl, phenyl, benzyl, 1-hydroxyethyl or mercaptomethyl, and $R^3$, $R^4$ and $R^5$ are all hydroxymethyl; R is hydrogen, $R^1$ and $R^2$ are both methyl, and $R^3$, $R^4$ and $R^5$ are all hydroxymethyl; R is hydroxy, hydroxymethyl, or carboxymethyl, $R^1$ and $R^2$ are both hydrogen, and $R^3$, $R^4$ and $R^5$ are all hydroxymethyl.

In the present invention, the transchelator functions additionally as a lyoprotectant and bulking agent. Most preferably, it is tricine, N-[tris(Hydroxymethyl)methyl] glycine, $C_6H_{13}NO_5$, chemical registry number 5704-04-1.

As a weight fraction of the weight of the active components of the kit, the transchelator fraction should be in the range of about 80% to about 99+%, more preferably in the range of about 90% to about 99%, most preferably about 95% to about 99%. The active components of the kit do not take into account inert ingredients and other kit components such as vials, caps, packaging material and the like.

5.2.3. Linker Molecule

The linker molecule serves to coordinately bind the radioisotope and to form a covalent bond to the targeting molecule. Additionally in the present invention, the linker molecule and/or the targeting molecule serve to protect the chemical reducing agent from oxidation, such that less reducing agent is required in the instant kit. There are two preferred classes of linker molecules, although others would be understood by those of average skill in the art having considered the present invention.

First, as described in European Patent Application PCT WO 94/10149 and in Schwartz, D. A. et al., 1991, Bioconjugate Chem. 2:333–336, there are hydrazyl pyridine derivatives of the general form

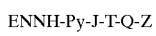

in which

E is an alkenyl group or represents $H_2$ in which case the compound is in an acid addition salt form, NNH is a hydrazyl fragment Py is a fragment of pyridine, $C_5H_3N$ J is selected from the group consisting of —CO—NH, —CO—O—, —CO—S— and —NH—CO—, T is an alkylene chain or, if J is —CO—NH—, T is the residue of an amino acid moiety, Q is a hydrophilic or cleavable moiety, and Z is an amine- and/or thiol reactive moiety.

Where E is alkenyl, it may be straight or branched lower alkenyl, of up to four carbon atoms.

The most preferred member of this class is the molecule in which E represents $H_2$, J is the group —C(═O)—NH, and bound to the NH group of J is the fragment: —$(CH_2)_3$—O—C(═O)—$CH_2$—Br, as depicted below:

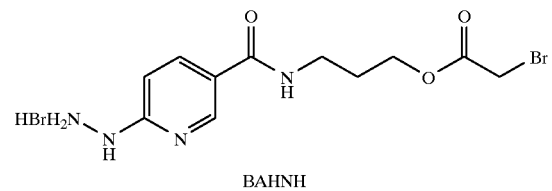

BAHNH

Other preferred members of this class are the following:
1. the molecule in which E represents $H_2$, J is the group C(=O)—O, and bound to the oxygen of J is the fragment $(CH_2)_3$—O—C(=O)—$CH_2$—Br.

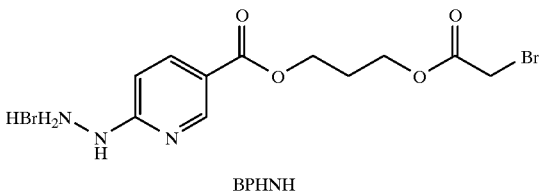

BPHNH 2. the molecule in which E represents $H_2$, J is the group —C(=O)—NH—, and bound to the NH group of J is the fragment —C—(—$(CH_2)_2$—C(=O)—OH)—C(=O)—O—$(CH_2)_3$—O—C(=O)—$CH_2$—Br

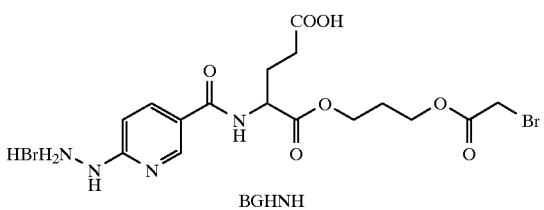

BGHNH 3. the molecule in which E represents $H_2$, J is the group —C(=O)—NH—, and bound to the NH group of J is the fragment —$(CH_2)_2$—S—C(=O)—$(CH_2)$—Br.

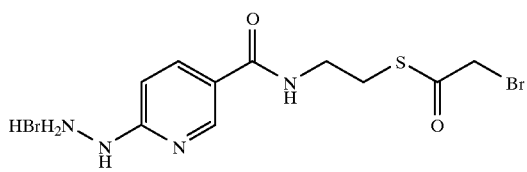

Second, as described in U.S. Pat. No. 5,326,856 and PCT publication WO93/21151, there are substituted thioureas of the formula:

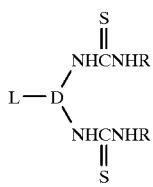

in which
L contains functionality to link to the targeting molecule
D is an alkyl backbone, cyclic alkyl backbone or aryl backbone group having the NHCSNHR groups at the 1,2-, 1,3-, 1,4-, or 1,5- (etc.) positions, and
R is H or a substituent with the general formula:

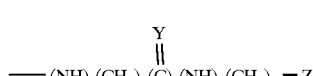

in which
a=0 or 1
b=0 to 10
c=0 or 1
if c=1 then, Y=S, O or $H_2$
d=0 to 2
e=0 to 10 and
Z=—H, $[—N(R')_3]^+X^-$, —$SO_3H$, —COOH, —OH, $H_2PO_3$;
in which X- is a counteranion such as a halide or an acid anion and R' is a C1 to C4 lower alkyl.

The most preferred member of this class is the molecule in which the NHCSNHR groups are in the 3,5 positions on a phenyl ring as depicted:

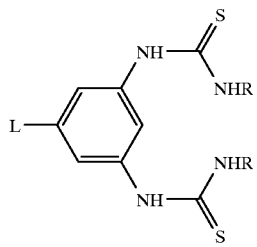

R is $[NHC(=O)CH_2]N^+[CH_3)_3] X^-$, in which $X^-$ is a halide ion and L is an acid hydrazide.

A preferred member of this class is the molecule in which the NHCSNHR groups are in the 3,5 positions, R is $[NHC(=O)CH_2]N^+[CH_3)_3] X^-$, in which $X^-$ is a halide ion and L is an acid hydrazide (linker BL14), see Coughlin and Belinka, U.S. Pat. No. 5,326,856. Another preferred member is as above except L is a carboxylic acid (linker BL1).

The weight of (linker molecule+targeting molecule) as a fraction of the entire weight of the active components of the kit is in the range of about 1% to about 20%, most preferably about 2% to about 3%. The active components of the kit do not take into account inert ingredients and other kit components such as vials, caps, packaging material and the like.

5.2.4. Targeting Molecule

The targeting molecule in the present invention is a subset of macromolecules having the ability to bind specifically to a target site and encompasses proteinaceous substances, including non-glycosylated proteins, glycoproteins, proteoglycans, etc., as well as peptidyl, polypeptidyl and glycopeptidyl substances. As such, the term includes polyclonal serum immunoglobulins, monoclonal antibodies, fragments of monoclonal antibodies having at least a portion of an antigen binding region including such as Fv, $F(ab')_2$, Fab, and Fab' fragments, single chain antibodies, chimeric or humanized antibodies, complementary determining regions (CDRs), etc., serum complement components, enzymes, cell surface histocompatibility antigens, cell surface receptors, receptor ligands, peptide or proteinaceous hormones, proteins or peptides which bind to cellular receptors, and molecular recognition units as that term is described in U.S. Pat. No. 5,196,510, incorporated herein by reference, and totally synthetic affinity reagents, as described in PCT/US94/00977, publication number WO94/18318, incorporated herein by reference. The targeting molecule has the ability to bind to a specific target and the targets encompass, for example, cells, tissues, organs, tumors and sites of infectious diseases, etc. These examples are merely illustrative and are not meant to limit the scope of possible targets.

5.2.5. One Pot Method for Preparing Lyophilized Formulation and Kit

The present invention provides a method for preparing a formulation as well as an instant kit comprising mixing a chemical reducing agent, a transchelator, and a conjugate molecule in aqueous solution and lyophilizing the resulting solution or lyophilizing an aqueous mixture of chemical reducing agent, transchelator, and conjugate molecule. The lyophilized mixture may be stored for over one year without a significant loss in activity. The lyophilized formulation or instant kit is combined with an aqueous solution of a radioisotope, such as Tc or Re, and the conjugate is radiolabelled.

Preferably, the chemical reducing agent comprises about 0.1% to 0.6% of the active components of the kit by weight, the transchelator comprises about 80% to 99+% of the active components of the kit by weight, and a conjugate, which comprises a targeting molecule covalently attached to a linker able to chelate a radiometal, such as Tc or Re and lyophilizing the mixture, comprises about a 1% to 4% fraction of the active components of the kit by weight. The active components of the kit do not take into account inert ingredients and other kit components such as vials, caps, packaging material and the like, known to those skilled in the art.

The transchelator is a compound of the formula:

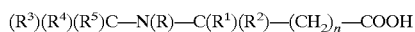

where R is hydrogen, hydroxy, alkyl, hydroxyalkyl, or alkylcarboxy, or R and $R^1$ together may form a mono-, di-, tri-, or tetra-methylene radical, or R and $R^2$ together may form a mono-, di-, tri-, or tetra-methylene radical, and $R^1$ and $R^2$ may be the same or different and are selected from hydrogen, hydroxy, alkyl, hydroxyalkyl, carboxy, alkylcarboxy, alkylamine, alkylthiol and aryl or $R^1$ and $R^2$ together may form a tetra- or penta-methylene radical, and $R^3$ and $R^4$ and $R^5$ may be the same or different and are selected from hydrogen, hydroxy, alkyl, hydroxyalkyl, carboxy and alkylcarboxy, provided that at least one of $R^3$, $R^4$ and $R^5$ is hydroxyalkyl, and n is equal to 0, 1 or 2.

Preferred alkyl and substituted alkyl groups for R are alkyl of 1 to 3 carbon atoms. Preferably, when $R^1$ and $R^2$ are alkyl or substituted alkyl, they are 1 to 4 carbon atoms. Preferred aryl groups are phenyl and benzyl. Preferably, when $R^3$ and $R^4$ and $R^5$ are alkyl or substituted alkyl groups they are 1 to 3 carbon atoms.

Preferably, at least one of R, $R^1$ and $R^2$ is hydrogen and at least one of $R^3$, $R^4$ and $R^5$ is hydroxymethyl. Other desirable compounds are those in which R, $R^1$ and $R^2$ are all hydrogen, $R^3$ is hydrogen, methyl or ethyl, and $R^4$ and $R^5$ are hydroxymethyl or 2-hydroxyethyl; R, $R^1$ and $R^2$ are all hydrogen, $R^3$ and $R^4$ are hydrogen or methyl, and $R^5$ is hydroxymethyl or 2-hydroxyethyl. Also desirable are compounds in which R and $R^1$ are both hydrogen, $R^2$ is methyl hydroxy, hydroxymethyl, carboxy, carboxymethyl, 2-carboxyethyl, phenyl, benzyl, 1-hydroxyethyl or mercaptomethyl, and $R^3$, $R^4$ and $R^5$ are all hydroxymethyl; R is hydrogen, $R^1$ and $R^2$ are both methyl, and $R^3$, $R^4$ and $R^5$ are all hydroxymethyl; R is hydroxy, hydroxymethyl, or carboxymethyl, $R^1$ and $R^2$ are both hydrogen, and $R^3$, $R^4$ and $R^5$ are all hydroxymethyl.

In the present invention, the transchelator functions additionally as a lyoprotectant and bulking agent. Most preferably, the transchelator/lyoprotectant/bulking agent is N-[tris (hydroxymethyl) methyl] glycine, $C_6H_{13}NO_5$, chemical registry number 5704-04-1. Preferably, the reducing agent is tin dichloride dihydrate. The lyophilized mixture can then be combined with an aqueous solution of radioactive metal, such as Tc or Re, wherein the linker chelates the radiometal. The aqueous solution can be water, saline, or any other pharmaceutically acceptable aqueous solution. This resultant radioactive mixture can then be used for in vivo treatment and/or diagnostics as well as for in vitro diagnostics.

Additionally, as a consequence of using a transchelator, such as tricine, as a lyoprotectant, as well as a transchelator, the dissolution of the lyophilized powder is rapid and particulate free and the immunoreactivity of the conjugate is unchanged.

In an embodiment of the instant kit, up to 10 mg/ml conjugate can be used in an instant kit formulation of the resent invention.

In a preferred embodiment the instant kit is formed by mixing about 36 mg tricine, 50 μg tin dichloride dihydrate, 0.2–1 mg conjugate, CYT-402 (Fab' fragment of mAb 15A8 covalently attached to linker BAHNH), 10 mM citrate, and 1 nM $Na_2EDTA$ in about 1.0 ml total volume, at about pH 5, and lyophilizing the mixture in one pot. The lyophilized kit is stable for months.

In another preferred embodiment, the instant kit comprises a lyophilized mixture of about 36 mg tricine, 50 μg tin dichloride dihydrate, 0.2–1 mg conjugate, CYT 422 (7E11C5 mAb covalently attached to linker BL14), 10 mM citrate, and 1 mM $Na_2EDTA$ at about pH 5 in one pot.

In yet another preferred embodiment of the present invention, the instant kit comprises a lyophilized mixture of about 36 mg tricine, 50 μg tin dichloride dihydrate, 0.2–1 mg conjugate, CYT 421 (Antibody B72.3 covalently attached to linker BL14), 10 mM citrate, and 1 mM $Na_2EDTA$ at about pH 5 in one pot.

The instant kit may further comprise inert ingredients and other kit components such as vials, packaging components and the like, which are well known to those skilled in the art.

The lyophilized instant kit of the present invention tested against a prior art formulation is shown in FIG. 2. FIG. 2 demonstrates the difference in incubation time required to achieve >95% incorporation of $^{99m}Tc$ by radioimmunoconjugate prepared using the lyophilized kit formulation of the present invention and by a fresh two pot method liquid formulation of the prior art.

6. Examples

In order to more fully illustrate the nature of the invention and the manner of practicing the same, the following examples are provided, which are not to be construed as limiting the remainder of the disclosure or the scope of the invention in any way whatsoever.

6.1 Tricine as a Lyoprotectant

According to the present invention, tricine is an excellent lyoprotectant since it is very difficult to crystallize dissolved tricine from frozen aqueous solutions. Thermal analyses demonstrated very clearly that a 20% w/w aqueous tricine solution froze and thawed without any eutectic behavior. Electrical resistance rose during freezing in a manner strongly characteristic of any system in which water separates as ice while solute continues merely to concentrate. Differential thermal analysis revealed a highly characteristic warming behavior of a sort always associated with the stepwise softening of a concentrated amorphous phase. Consecutive glass transitions were clearly identified. A first glass transition occurred between ca −60° C. and ca −45° C. and a second subsequent glass transition occurred between ca −40° C. and ca −32° C. In addition, a characteristic melting endotherm began at −25° C. and ends at −2° C.

Glass transition temperatures were identified also from the electrical resistance recordings and seemed to correspond rather nicely to those determined by DTA.

Similar results were found using cryomicroscopy and freeze-drying microscopy. A 5 μl volume of a 5% wt/wt aqueous tricine solution was put on a cryomicroscope and frozen at −10° C., with seeding by indirect contact with colder forceps. The frozen preparation was subjected to temperatures of −8, 10, −12.5, −15 and −20° C. each for 15 to 30 minutes. The development of an ice phase and the attendant segregation of an implicitly concentrated aqueous tricine phase was observed. Intermittent observation failed to reveal any corresponding crystallization of tricine. No nucleation of any additional crystalline phase was detected at any time. Concentrated amorphous aqueous tricine appeared to persist as such at all temperatures to −20° C. Next the sample was seeded with dry tricine crystals. Tricine crystal growth was seen to begin at the edge of the preparation and progressed very slowly beneath the glass cover slip. The tricine crystals dissolved during a warming cycle to −3° C. and did not reappear when the preparation was again cooled. The freeze-drying process was also studied on a Freeze-Drying microscope. Freeze-drying of a 5% wt/wt aqueous tricine solution was seen to proceed with retention (fine structure was retained) at −50, −45, and −40° C. and with collapse (fine structure was not retained) at −35 and −30° C.

All the experimental findings point to the consistent freezing/thawing behavior on the part of aqueous tricine solutions and to the further consistency of their freezing and freeze-drying behavior. Only a deliberate intervention altered the pattern. Aqueous tricine solutions froze with the development of an amorphous tricine concentrate that hardened to a glass with sufficient cooling, which could be softened with sufficient warming. One safely concludes that aqueous tricine solutions demonstrate: i) "non-eutectic" freezing, and ii) non-eutectic freeze-drying behavior governed by the properties of the amorphous tricine concentrate.

6.2 $^{99m}$Tc Radioconjugate Prepared Using the One Pot Lyophilized Kit

An instant kit was formulated for one step radiolabeling which on combination with $^{99m}$Tc provided very fast labeling kinetics. The instant kit comprised a mixture of a reducing agent, i.e., tin dichloride dihydrate, a transchelator and lyoprotectant, i.e., tricine, and an immuno-conjugate. The conjugate was comprised of a targeting molecule, i.e., monoclonal antibody Fab' 15A8 [White et al., 1985, Cancer Res. 45:1337–1343; Rosenstraus et al., 1991, Cancer Res. 51:5744–5751; U.S. Pat. No. 5,032,521] covalently attached to a linker molecule, in which the linker was a hydrazyl pyridine, i.e., BAHNH [Schwartz et al., PCT WO 94/10149], shown below.

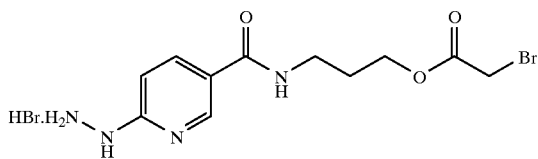

6.2.1 $^{99m}$mTc Incorporation Using the Lyophilized Instant Kit of the Invention F(ab')$_2$ fragments of 15A8 were generated by pepsin digestion of mAb 15A8 as previously described [Rea et al., 1993, J. Immunol. Methods 157:165–173]. BAHNH (Acetic acid, bromo-,3-{[(6-hydrazino-3-pyridinyl)carbonyl]amino}propyl ester monohydrobromide) was synthesized by Johnson-Matthey (West Chester, Pa.) as described in PCT WO 94/10149 and was used without further purification.

Conjugation to form CYT-402: 15A8 F(ab')$_2$ fragments in PBS-EDTA (10 mM Phosphate, 150 mM NaCl, 1 mM EDTA, pH 7) were concentrated to 5–20 mg/ml using an Amicon® Centricon-10® concentrator (W. R. Grace & Co., Beverly, Mass.) or Amicon® Stirred Ultrafiltration Cell with a YM10 membrane. The conjugation was initiated by reduction of the F(ab')$_2$ with an 8 molar excess of dithiolthreitol (DTT) to Fab' for 14–18 hours at room temperature in the dark. The reduction was monitored by isocratic size exclusion HPLC using a TSK-3000 SW$_{XL}$ column (TOSOHASS, Philadelphia, Pa.) equilibrated with PBS/1 mM EDTA, pH 6. The DTT was not removed from the conjugation mixture after reduction. The reduced F(ab')$_2$-DTT mixture was conjugated with a 3 molar excess of BAHNH to the DTT thiol content. BAHNH was added as a 30 mM-100 mM solution in water and the pH adjusted to 6.0 with 1 M NaOH. The F(ab')-DTT-BAHNH mixture was incubated for 16–23 hours at 15–30° C. after purging the reaction vessel with nitrogen or argon. The CYT-402 conjugate (15A8-Fab'-BAHNH) was purified from the mixture by size exclusion HPLC using a preparative or analytical grade Superose-12 column (Pharmacia, Piscataway, N.J.). The conjugation mixture load volumes were 3% of total bed volume. The column was eluted at a linear flow rate of 0.5 cm/min with 10–20 mM Na citrate, pH 5.0 containing 1–2 mM EDTA. The Fab'-BAHNH conjugate was concentrated to 2–5 mg/ml using an Amicons Centricons concentrator. The protein concentration of the samples was determined by either extinction coefficients of $E_{280,mg/ml}$ of 1.36 for 15A8-2a or by the Biorad Protein Determination Assay as described by the manufacturer using 15A8-2a protein reference standards.

4,4' DTDP Residual Thiol Assay: Samples to be examined were diluted in a total volume of 0.9 mL thiol assay buffer (100 mM Phosphate pH 7, 1 mM EDTA) and UV absorbance at 280 nm and 324 nm was determined. 100 μL of 2 mM 4,4'-Dithiodipyridyl in water was added to the diluted sample and the absorbance at 324 nm was again determined. The thiol concentration was calculated using the published extinction coefficient of 4-thiol pyridone ($E_{324,M}$=23,000) after subtraction of the pre-DTDP OD$_{324}$ absorbance from the post-DTDP OD$_{324}$ absorbance. The number of thiols per antibody fragment was determined by dividing the thiol concentration (μM) by the protein concentration (μM).

o-Sulfonic Benzoic Acid Hydrazine Assay: Samples to be examined were diluted into 1 mL of o-sulfonic benzoic acid (Eastman Kodak, Rochester, N.Y.) 10.4 mg/100 mL 0.1 M acetate, pH 4.73. The hydrazine concentration was calculated using an extinction coefficient of $E_{343,M}$=26,500. The molecular substitution ratio (MSR) of hydrazine conjugated to antibody was determined by dividing the hydrazine concentration (μM) by the protein concentration (μM) as determined by a Biorad protein determination assay.

Radiolabeling of CYT-402: A mixture of CYT-402 conjugate, tin dichloride dihydrate, and tricine in an aqueous solution was lyophilized. The lyophilized mixture was subsequently resuspended with an aqueous solution of radioactive $^{99m}$Tc, and upon incubation, in less than about 5 minutes, greater than 95% incorporation of $^{99m}$Tc by the conjugate was observed.

Radiopurity of the radiolabelled Fab' fragments was determined by Instant Thin Layer Chromatography (ITLC-SG, Gelman, Ann Arbor, Mich.). Saline, methylethylketone and IAW (isopropanol:ammonia:water 2:1:5) were used for mobile phases to determine percent incorporation, free pertechnetate levels and colloid, respectively. ITLC strips were cut at $R_f=0.5$.

Results of $^{99m}$Tc incorporation are presented in FIG. 3. As shown in FIG. 3, when an aqueous solution of $^{99m}$TCO$_4$ was combined with the lyophilized mixture, >95% Tc was incorporated into the conjugate in less than 5 minutes.

In contrast, the two pot method of the prior art, i.e., EP 0569132 A1, (where the chemical reducing agent and lyoprotectant-transchelator are lyophilized together, then combined with radiolabel and subsequently added to a liquid formulation of the conjugate), required over 75 minutes to incorporate >95% Tc, at loadings of 50–200 mCi Tc per 1 mg conjugate, which is typical of clinical situations. Additionally, the resultant radioconjugate prepared according to this prior art reference might need to be filtered to remove any aggregate particles formed, prior to administration.

Moreover, as seen in FIG. 3, using the present invention, good speed and efficiency of labeling was obtained even with increasing levels of radiolabel, in the range of 50–200 mCi/mg immuno-conjugate.

However, EP 0 569 132 A1 discloses that using the two pot tricine labeling method, >90% Tc is incorporated in less than 5 minutes, contradicting the present inventors' results using this method. In contradistinction to the results obtained using the present invention, these two-pot experiments showing rapid labeling were performed with $^{99m}$Tc at a specific activity of only 3 mCi/mg conjugate, far less than what is clinically required, which preferably is 50–200 mCi/mg conjugate. Furthermore, at greater specific activities (140 mCi/mg), 95% incorporation was reported after a 75–90 minute incubation. Thus, it is an important advantage of the present invention that high specific activity (50–200 mCi/mg) radiolabeling can be achieved in less than 5 minutes.

6.2.2 Long Term Stability of Lyophilized Mixture

The lyophilized mixture of tricine, tin, and conjugate prepared as described in Section 6.2 was stored at 2–8° C. or 25° C. for extended periods of time and still retained activity. As shown in Table I the same formulation of conjugate, either as a lyophilized mixture with transchelator and tin dichloride dihydrate or as an aqueous mixture, was stored at 2–8° C. or 25° C. for up to 14 months. The differentially stored formulations were subsequently tested for efficiency of radiolabeling by measuring percent incorporation of radiolabel into the conjugate, percent pertechnetate, percent radiolabelled transchelator, and percent colloid formation. These results are presented in Table I and in FIG. 4.

TABLE I

| TIME | % INCP[1] | % TcO$_4$ | % Tc-Tricine | % COLLOID |
|---|---|---|---|---|
| LIQUID FORMULATION AT 2–8° C. | | | | |
| Initial | 96.21 ± 0.31 | 1.10 ± 0.74 | 2.69 ± 1.05 | Not Done |
| 1 Week | 96.86 ± 0.27 | 1.33 ± 0.16 | 1.81 | 9.13 ± 8.80 |
| 8 Weeks | 87.77 ± 0.15 | 0.76 ± 0.18 | 11.48 ± 0.19 | 2.38 ± 0.23 |
| 3 No. | 87.56 ± 0.30 | 0.59 ± 0.01 | 11.85 ± 0.32 | 4.66 ± 0.80 |
| 5 Mo. | 81.96 ± 0.63 | 0.44 ± 0.18 | 17.60 ± 0.45 | 3.02 ± 1.05 |
| 14 Mo. | 70.57 ± 0.69 | 0.19 ± 0.05 | 29.20 ± 0.08 | 0.60 ± 0.14 |
| LIQUID FORMULATION AT 25° C. | | | | |
| Initial | 96.21 ± 0.31 | 1.10 ± 0.74 | 2.69 ± 1.05 | Not Done |
| 1 Week | 94.72 ± 0.16 | 2.05 ± 0.24 | 3.23 | 1.43 ± 0.04 |

TABLE I-continued

| TIME | % INCP[1] | % TcO$_4$ | % Tc-Tricine | % COLLOID |
|---|---|---|---|---|
| 8 Weeks | 64.21 ± 1.08 | 0.97 ± 0.04 | 34.82 ± 0.41 | 2.61 ± 0.16 |
| 3 Mo. | 55.93 ± 0.11 | 1.13 ± 0.06 | 42.94 ± 0.05 | 2.42 ± 0.71 |
| 5 Mo. | 53.72 ± 0.34 | 2.30 ± 1.34 | 43.98 ± 1.68 | 7.80 ± 8.30 |
| 14 Mo. | Not Done | Not Done | Not Done | Not Done |
| LYOPHILIZED FORMULATION AT 2–8° C. | | | | |
| Initial | 98.66 ± 0.11 | 1.53 ± 0.37 | 0.82 ± 0.49 | 8.32 ± 1.46 |
| 1 Week | 98.22 ± 0.01 | 0.30 ± 0.08 | 1.49 ± 0.08 | 2.29 ± 0.10 |
| 8 Weeks | 98.71 ± 0.23 | 0.37 ± 0.17 | 0.92 ± 0.39 | 5.12 ± 0.58 |
| 5 Mo. | 98.03 ± 0.27 | 0.37 ± 0.22 | 1.61 ± 0.05 | 2.58 ± 0.56 |
| 14 Mo. | 98.00 ± 0.16 | 0.03 ± 0.07 | 1.97 ± 0.02 | 1.57 ± 0.11 |
| LYOPHILIZED FORMULATION AT 25° C. | | | | |
| Initial | 98.66 ± 0.11 | 0.53 ± 0.37 | 0.82 ± 0.49 | 8.32 ± 1.46 |
| 1 Week | 98.31 ± 0.18 | 0.23 ± 0.05 | 1.47 ± 0.13 | 4.99 ± 1.63 |
| 8 Weeks | 98.58 ± 0.15 | 0.21 ± 0.04 | 1.22 ± 0.10 | 5.14 ± 1.53 |
| 5 Mo. | 98.37 ± 0.10 | 0.23 ± 0.04 | 1.40 ± 0.08 | 2.77 ± 1.63 |
| 14 Mo. | 97.21 ± 0.41 | 0.02 ± 0.04 | Not Done | 1.76 ± 0.40 |

[1]Percent incorporation into the conjugate.

Table I demonstrates the long term stability of the lyophilized mixture of tricine, tin dichloride dihydrate, and conjugate stored at either room temperature or at 2–8° C. as compared to liquid formulations stored at room temperature or 2–8° C. Methods for testing $^{99m}$Tc incorporation, percent pertechnetate, percent labeled transchelator, and percent colloid formation herein are as described by Robbins, 1984, Chromatography of Technetium-99$^m$ Radiopharmaceuticals: A Practical Guide., Society of Nuclear Medicine, NY, N.Y.

As demonstrated in Table I and FIG. 4 over a 14 month period, the liquid formulations have shown a continuous decline in activity even when stored at 2–8° C. (by 8 weeks the percent incorporation fell below the required specification (90%) of the conjugate for use in vivo). In contrast, the formulations prepared using the present one pot lyophilization method have shown excellent stability.

The lyophilized formulation according to the present invention, after 14 months at 25° C. still shows excellent stability by every parameter measured: HPLC and SDS-PAGE, immunoreactivity, protein concentration, Isoelectric focusing (IEF), hydrolysis product formation and linker labeling functional group quantitation. The protocols for measuring these parameter are well known in the art or are as follows. For example, 15A8 immunoreactivity was determined by a radioimmunoassay using live ME180 cells. Trypsinized ME180 cells were washed and serially diluted to $2\times10^6$ cells/mL in MEM containing 10 mM HEPES and 10% fetal bovine serum (MEM-FBS). To each cell dilution was added $1\times10^5$ cpm of $^{99m}$Tc-labeled 15A8. The cells were incubated for 1 hour at 4° C. and were collected by centrifugation, washed and counts obtained in a gamma counter. The immunoreactive fraction was determined by plotting the inverse of the bound fraction versus the inverse of the cell concentration. The Y intercept, the fraction of radioactivity at infinite antigen excess, was determined by linear regression analysis.

Table II shows a comparison of the lyophilized formulation of conjugate, transchelator, and chemical reducing agent, (CYT-402, tricine, and tin dichloride dihydrate), or as an aqueous conjugate preparation, stored at 2–8° C. or 25° C. These formulations were tested at the various time points for the various parameters listed after labeling with $^{99m}$Tc.

TABLE II

CYT-402 INSTANT KIT WITH TRICINE AND TIN LYOPHILIZED

LIQUID FORMULATION AT 2–8° C.

| ASSAY | | INITIAL* | T = 1 WEEK | T = 8 WEEKS | T = 3 MONTHS | T = 5 MONTHS | T = 14 MONTHS |
|---|---|---|---|---|---|---|---|
| BAHNH-ALC | MOLE RATIO | ND | ND | ND | ND | 0.07 ± 0.02 | 0.24 ± 0.04 |
| MONOMER SDS-PAGE | % BANDS | ND 2 MAJOR @ 25000D 1 MINOR @ 50000D | 100 ± 0.00 2 MAJOR @ 25000D 1 MINOR @ 50000D | 94.81 ± 0.65 2 MAJOR @ 25000D 1 MINOR @ 50000D | 95.43 ± 0.43 2 MAJOR @ 25000D 1 MINOR @ 50000D | 96.38 ± 43 2 MAJOR @ 25000D 1 MINOR @ 50000D | 93.33 ± 1.86 2 MAJOR @ 25000D 1 MINOR @ 50000D |
| IEF | pI | ND 2 MAJOR BANDS pI 7.0, 6.4 | 2 MAJOR BANDS pI 7.0, 6.4 | 2 MAJOR BANDS pI 7.0, 6.4 | 2 MAJOR BANDS pI 7.0, 6.4 | 2 MAJOR, 1 MINOR BAND pI 7.0, 6.4, 6.3 | 2 MAJOR, 1 MINOR BAND |
| PROTEIN (IN CUVETTE) | mg/mL μM/L | 2.3 ± 0.10 4.620 | 1.75 ± 0.24 3.50 ± 0.48 | 2.26 ± 0.04 4.66 ± 0.28 | 1.80 ± 0.10 3.60 ± 0.21 | 1.89 ± 0.11 3.78 ± 0.23 | 1.73 ± 0.05 3.46 ± 0.09 |
| PROTEIN HYDRAZINE | μM/L | 11.472 ± 0.37 | 11.23 ± 0.03 | 10.08 ± 0.43 | 9.91 ± 0.08 | 8.57 ± 0.21 | 6.72 ± 0.21 |
| MSR | | 2.483 ± 0.081 | 3.24 ± 0.44 | 2.17 ± 0.04 | 2.76 ± 0.18 | 2.27 ± 0.19 | 1.94 ± 0.01 |
| pH | | ND | 5.09 ± 0.05 | 5.05 ± 0.01 | 4.99 ± 0.01 | 5.06 ± 0.01 | ND |
| RADIOLABELING | % INCP | 96.21 ± 1.89% | 96.86 ± 0.28 | 87.77 ± 0.15 | 87.56 ± 0.30 | 81.96 ± 0.63 | 70.57 ± 0.69 |
| IMMUNORX | % STD % % OF STD | 81.3% 88.5% 91.9% | 70.9% 77.2% 91.8% | 79.6% 79.6% 100.00 | ND ND ND | ND ND ND | ND ND ND |

LIQUID FORMULATION AT 25° C.

| ASSAY | | T = 1 WEEK | T = 8 WEEKS | T = 3 MONTHS | T = 5 MONTHS |
|---|---|---|---|---|---|
| BAHNH-ALC | MOLE RATIO | ND | ND | ND | <0.05 |
| MONOMER SDS-PAGE | % BANDS | 100 ± 0.00 2 MAJOR @ 25000D 1 MINOR @ 50000D | 86.69 ± 4.38 2 MAJOR @ 25000D 1 MINOR @ 50000D | 88.95 ± 4.31 2 MAJOR @ 25000D 1 MINOR @ 50000D | 94.24 ± 0.65 2 MAJOR @ 25000D 1 MINOR @ 50000D |
| IEF | pI | 2 MAJOR BANDS pI 7.0, 6.4 | 3 MAJOR BANDS pI 7.0, 6.4, 6.2 | 3 MAJOR BANDS pI 7.0, 6.4, 6.2 | 3 MAJ/4 MIN BANDS pI 7.0, 6.4, 6.2 |
| PROTEIN (IN CUVETTE) PROTEIN | mg/mL μM/L | 1.85 ± 0.02 3.70 ± 0.03 | 2.15 ± 0.01 4.34 ± 0.03 | 1.70 ± 0.04 3.41 ± 0.08 | 1.73 ± 0.07 3.46 ± 0.14 |

TABLE II-continued

| | | CYT-402 INSTANT KIT WITH TRICINE AND TIN LYOPHILIZED | | |
|---|---|---|---|---|
| HYDRAZINE | μM/L | 10.55 ± 0.08 | 5.64 ± 1.36 | 4.00 ± 1.71 | 2.80 ± 0.53 |
| MSR | | 2.85 ± 0.00 | 1.30 ± 0.32 | 1.18 ± 0.53 | 0.81 ± 0.19 |
| pH | | 5.10 ± 0.01 | 5.01 ± 0.06 | 4.99 ± 0.00 | 5.11 ± 0.02 |
| RADIOLABELING | % INCP | 94.72 ± 0.16 | 64.21 ± 1.08 | 55.93 ± 0.11 | 53.72 ± 0.34 |
| | % | 70.4% | 76.4 ± 0.4% | ND | ND |
| IMMUNORX | STD % | 77.2% | 79.6% | ND | ND |
| | % OF STD | 91.2% | 96.0 ± 0.5% | ND | ND |

| | | LYOPHILIZED FORMULATION AT 2–8° C. | | | | |
|---|---|---|---|---|---|---|
| ASSAY | | INITIAL* | T = 1 WEEK | T = 8 WEEKS | T = 5 MONTHS | T = 14 MONTHS |
| BAHNH-ALC | MOLE RATIO | ND | ND | ND | NONE DETECTED | NONE DETECTED |
| MONOMER | % | 97.45 ± 0.34% | 100.00 ± 0.00 | 97.16 ± 0.18 | 97.63 ± 0.02 | 99.17 ± 1.18 |
| SDS-PAGE | BANDS | 2 MAJOR @ 25000D 1 MINOR @ 50000D | 2 MAJOR @ 25000D 1 MINOR @ 50000D | 2 MAJOR @ 25000D 1 MINOR @ 50000D | 2 MAJOR @ 25000D 1 MINOR @ 50000D | 2 MAJOR @ 25000D 1 MINOR @ 50000D |
| IEF | pI | ND | 3 MAJOR BANDS pI 7.0, 6.4, 6.2 | 3 MAJOR BANDS pI 7.0, 6.4, 6.2 | 3 MAJOR BANDS pI 7.0, 6.4, 6.2 | 3 MAJOR BANDS |
| PROTEIN | mg/VIAL | 1.09 ± 0.07 | 0.87 ± 0.09 | 0.95 ± 0.06 | 0.95 ± 0.05 | 0.81 ± 0.03 |
| (IN CUVETTE) PROTEIN | μM/L | 4.350 | 3.50 ± 0.35 | 3.79 ± 0.23 | 3.80 ± 0.21 | 3.23 ± 0.13 |
| HYDRAZINE | μM/L | 10.057 ± 0.29 | 8.99 ± 0.59 | 7.68 ± 0.72 | 8.34 ± 1.33 | 8.64 ± 0.75 |
| MSR | | 2.312 ± 0.067 | 2.57 ± 0.09 | 2.02 ± 0.07 | 2.19 ± 0.23 | 2.68 ± 0.13 |
| pH | | 4.91 ± 0.01 | 4.94 ± 0.00 | 4.92 ± 0.01 | 5.02 ± 0.00 | |
| RADIOLABELING | % INCP | 98.66 ± 0.10% | 98.22 ± 0.01 | 98.71 ± 0.23 | 98.03 ± 0.27 | 98.00 ± 0.16 |
| | % | 80.6% | 79.7% | 85.2% | 77.7% | ND |
| IMMUNORX | STD % | 88.5% | 77.2% | 79.6% | ND | ND |
| | % OF STD | 91.1% | 103.2% | 107.1% | ND | ND |

TABLE II-continued

CYT-402 INSTANT KIT WITH TRICINE AND TIN LYOPHILIZED

LYOPHILIZED FORMULATION AT 25° C.

| ASSAY | | T = 1 WEEK | T = 8 WEEKS | T = 5 MONTHS | T = 14 MONTHS |
|---|---|---|---|---|---|
| BAHNH-ALC | MOLE RATIO | ND | ND | NONE DETECTED | NONE DETECTED |
| MONOMER | % | 100 ± 0.00 | 97.09 ± 0.13 | 98.09 ± 0.06 | 97.94 ± 0.37 |
| SDS-PAGE | BANDS | 2 MAJOR @ 25000D 1 MINOR @ 50000D 3 MAJOR BANDS | 2 MAJOR @ 25000D 1 MINOR @ 50000D 3 MAJOR BANDS | 2 MAJOR @ 25000D 1 MINOR @ 50000D 3 MAJOR BANDS | 2 MAJOR @ 25000D 1 MINOR @ 50000D 3 MAJOR BANDS |
| IEF | PI | pI 7.0, 6.4, 6.2 | pI 7.0, 6.4, 6.2 | pI 7.0, 6.4, 6.2 | |
| PROTEIN | mg/VIAL | 0.94 ± 0.09 | 1.02 ± 0.05 | 0.92 ± 0.03 | 0.79 ± 0.01 |
| (IN CUVETTE) PROTEIN | μM/L | 3.75 ± 0.14 | 4.04 ± 0.22 | 3.70 ± 0.14 | 3.16 ± 0.06 |
| HYDRAZINE | μM/L | 8.78 ± 0.13 | 7.40 ± 0.05 | 8.89 ± 0.35 | 7.55 ± 0.05 |
| MSR | | 2.59 ± 0.06 | 1.83 ± 0.08 | 2.40 ± 0.00 | 2.39 ± 0.02 |
| pH | | 4.93 ± 0.01 | 4.93 ± 0.00 | 5.04 ± 0.00 | ND |
| RADIOLABELING | % INCP | 98.31 ± 0.18 | 98.58 ± 0.15 | 98.37 ± 0.10 | 97.21 ± 0.41 |
| IMMUNORX | % | 60.9% | 98.4% | 72.7% | ND |
| | STD % | 77.2% | 79.6% | ND | ND |
| | % OF STD | 78.9% | 123.6% | ND | ND |

ND = NOT DONE

*This material was prepared, placed in a vial and lyophilized. The lyophilized vials were stored at 2–8° C. for 4 weeks until this study was initiated.

6.2.3 Stannous Stability

In an additional experiment, radiolabeling characteristics of formulations containing varying amounts of stannous dichloride dihydrate versus varying amounts of immunoconjugate were studied. Results are presented in Table III. When no immunoconjugate was included in the lyophilized tricine/tin formulation, more tin was required (100 µg) to achieve even minimal $^{99m}$Tc incorporation (41%). When 0.2 mg of immunoconjugate was lyophilized with tricine and tin, the highest concentration of tin studied (100 µg) resulted in 84% incorporation. However, surprisingly when 0.5 mg of immunoconjugate was lyophilized with tricine and tin, even the lowest concentration of tin studied (25 µg) resulted in 90% incorporation. It appeared that increasing concentrations of immunoconjugate helped to stabilize the stannous ion in the lyophilized formulation for effective reduction of technetium and subsequent high incorporation into an immunoconjugate.

TABLE III

SUMMARY OF RADIOLABELING DATA ON CYT-402 LYOPHILIZED PROTEIN/TIN MATRIX STUDY

| TIN | % INCP | % TcO$_4$ | % Tc-Tricine | % COLLOID |
|---|---|---|---|---|
| TRICINE (36 MG) LYOPHILIZED WITH TIN AND 0 mg CYT-402* | | | | |
| 25 µg | 3.35 ± 0.26 | 88.33 ± 0.14 | 8.32 ± 0.40 | 0.04 ± 0.02 |
| 50 µg | 3.44 ± 0.43 | 87.59 ± 0.86 | 8.98 ± 0.43 | 0.52 ± 0.24 |
| 100 µg | 41.00 ± 20.23 | 37.20 ± 17.12 | 21.81 ± 3.10 | 1.87 ± 1.03 |
| TRICINE (36 MG) LYOPHILIZED WITH TIN AND 0.2 mg CYT-402 | | | | |
| 25 µg | 38.66 ± 19.24 | 42.06 ± 7.11 | 19.29 ± 12.13 | 2.69 ± 1.22 |
| 50 µg | 52.25 ± 0.00 | 28.05 ± 12.08 | 19.71 ± 12.09 | 4.18 ± 0.48 |
| 100 µg | 84.29 ± 2.51 | 1.73 ± 0.43 | 13.98 ± 2.94 | 5.66 ± 0.42 |
| TRICINE (36 MG) LYOPHILIZED WITH TIN AND 0.5 mg CYT-402 | | | | |
| 25 µg | 90.62 ± 0.05 | 2.61 ± 0.19 | 6.78 ± 0.23 | 8.39 ± 3.04 |
| 50 µg | 86.18 ± 5.26 | 2.95 ± 2.42 | 10.87 ± 2.84 | 8.06 ± 2.79 |
| 100 µg | 89.98 ± 1.84 | 0.76 ± 0.46 | 9.27 ± 2.30 | 8.00 ± 1.63 |

*The 0 mg CYT-402 vials were incubated with $^{99m}$TC for 15 minutes, then CYT-402 liquid formulation was added for a final specific activity of 50 mCi/mg.

6.2.4 Non-Toxicity of Tricine

Tricine was tested to determine its toxicity in mice and therefore suitability as a component of a pharmaceutical composition. 10 mice were injected i.v. with a single dose of 2.34 mg/kg body weight of tricine in saline solution. This dose represents 4.5 times, assuming a 70 kg human, of an amount of tricine used in a commercial embodiment of the invention. One mouse died for unknown reasons less than one day after receiving the injection. The remaining 9 mice survived until dissection, which was 7 days for 4 mice and 14 days for the remaining 5 mice. The body weights of the test subjects rose slowly during the study at a rate similar to control, non-injected mice. Furthermore, the weights of the spleen, liver, and kidneys were unchanged from 7 to 14 days, and were similar to that of the controls. There were no signs of toxicity in the internal organs or in the activity or appearance of the mice. Thus, in this study tricine appeared to have no toxic side effects in mice, even when administered at a dose 4.5 times the clinical dose.

6.2.5 In Vivo Clearance Rates: Comparison Between a Liquid Formulation and a Formulation Prepared Using the Present Lyophilized Kit A side by side comparison of in vivo clearance rates between two formulations of a $^{99m}$Tc-labeled conjugate, CYT-402 (mAb 15A8 Fab'-BAHNH), was done. The radioconjugates were prepared using two different ways, the two pot method of the prior art and the one pot method of the present invention. In both protocols the same transchelator, reducing agent and conjugate were used and in the same amounts. In each case, 36 mg of tricine, 50 µg of stannous dichloride dihydrate, and 1 mg CYT-402 were used.

In the two pot method, the $^{99m}$Tc was first combined with the reducing agent and transchelator. Next, this mixture was combined with the conjugate molecule, in a liquid formulation.

In the one pot method of the present invention the reducing agent, the transchelator, and the conjugate were mixed together and lyophilized. This lyophilized mixture was then mixed with an aqueous solution of $^{99m}$Tc.

After the addition of the $^{99m}$Tc to the conjugates, the solutions were incubated such that >90% of the $^{99m}$Tc was incorporated into the conjugate molecules. The biodistribution characteristics of the resultant radioconjugates prepared by the two methods were compared. Athymic (nu/nu) Swiss background nude mice (Taconic Farms, Germantown, N.Y.) bearing MCF-7 (American Type Culture Collection, Rockville Md.) xenographs were used to determine the biodistribution, pharmacokinetics and tumor imaging of the conjugates. Mice were injected i.v. with 20 µg of Fab' fragments containing 0.5–1 mCi $^{99m}$Tc. Mice were dose calibrated and bled for initial blood and whole body pharmacokinetics immediately after injection of the $^{99m}$Tc-Fab' fragments. Blood pharmacokinetics and whole body clearances were determined by bleeding or dose calibrating the mice at 2,4,6, and 24 hours post-injection. Dissected tissues were weighted and the amount of $^{99m}$Tc determined by gamma counting. Data were represented as the ratio of the cpm/g in each organ compared to the cpm/g in blood (organ/blood ratio) and the percentage dose injected (ID) per gram in each organ. The biological half-life (whole body) of Tc was calculated assuming a single experimental decay function from mice dose calibration data. Similarly, the blood half-life was calculated from the average percentage ID/g in blood at 2, 4, 6, and 24 hours.

The results of this comparison are shown in FIGS. 5a and 5b and FIGS. 6a–d.

As seen in FIG. 5a, there was no discernable difference in the rate of whole body clearance between the two separately prepared radioconjugates in tumor bearing mice or normal mice. FIG. 5b shows similar results for blood clearance.

Additionally, FIGS. 6a–d show that there were no significant differences in the organ distribution between the two formulations.

These results suggest that there is no difference in the in vivo behavior of the two differently prepared radioconjugates in whole body/blood clearance and that the specificity of the radioconjugate produced by the one pot method of the present invention appeared unchanged in comparison to the two pot method.

6.3 $^{99m}$Tc Labeling of CYT-421

The labeling of immunoconjugate CYT-421, mAb B72.3-linker BL14 (BL14 is described in Section 5.2.3, supra) with different transchelators and at different pH was determined. A sample of purified CYT-421 was split into three different aliquots. One aliquot was adjusted to pH 6.0, a second aliquot was adjusted to pH 7.0 and a third aliquot was maintained at pH 5.0 (unadjusted pH). These aliquots were subsequently labeled with $^{99m}$Tc at three different specific activities, 10, 25, and 50 mCi/mg conjugate with four different transchelators; an AN-MDP® medronate kit (commercially available from CIS-US, Inc.); TechneScan®

PYP® sodium pyrophosphate kit (commercially available from Mallinckrodt, Inc.); Glucoscan® glucoheptonate kit (commercially available from DuPont/Merck); and tricine; and $^{99m}$Tc incorporation was measured. The results are summarized in FIGS. 7a–d.

Using an AN-MDP® kit, the conjugate incorporated less than 5% of the radiolabel at all specific activities and pH values tested. Using a TechneScan® PYP® kit, the conjugate incorporated less than 10% of the radiolabel for all specific activities and pH values tested. Using a Glucoscan® kit, the conjugate incorporated maximally less than 90% of the radiolabel for all specific activities and pH values tested. Tricine was the most effective transchelator. The resultant immunoconjugate incorporated at a minimum greater than 88% of the radiolabel, maximal incorporation of 97% occurred at pH 6.5. Most importantly, only tricine was effective as a transchelator for achieving greater than 95% incorporation by CYT-421 in the preferred pH range of 5.2–6.4.

tion at pH 6 (concentration is approximately, 5 mg of antibody per 1 ml of buffer) was added to a reaction vial which was wrapped in aluminum foil. Then, 16 mg of sodium periodate dissolved in approximately 100 µl of PBS buffer was added in one portion. The resultant mixture was allowed to stand in the dark for 1 hour at room temperature. The reaction solution was divided into 2 equal aliquots and each was diluted to a total volume of 2.5 ml by adding 0.1 M acetate buffer at pH 5. The two individual samples of oxidized antibody were desalted on NAP-25 (Pharmacia, Piscataway, N.J.) columns which had been previously been equilibrated with 0.1 M acetate buffer at pH 5. The eluted oxidized antibody was concentrated on an Amicon® Centraprep®-30 cartridge system (W. R. Grace & Co., Beverly, Mass.) to a volume of approx. 5 mg antibody per ml of buffer.

The solution of approximately 15 mg CYT-351 oxidized antibody in acetate buffer, pH 5, was stirred in a reaction vial as 4.27 mg of CYT-395 chelator (see below) dissolved in 160 µl of water was added in one portion.

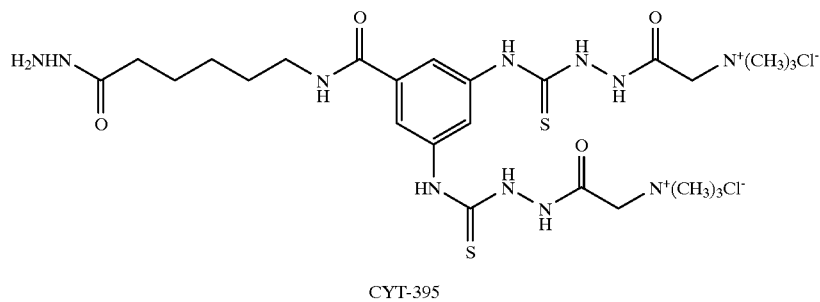

CYT-395

6.4 One Pot Formulation of CYT-421

A lyophilized instant kit containing transchelator, reducing agent, and conjugate was formulated containing 1 mg conjugate CYT-421, 36 mg tricine, 50 µg tin dichloride dihydrate, 10 mm citrate and 1 mM Na$_2$EDTA in 1 ml total volume. Another kit was formulated with sodium glucoheptonate in place of tricine, in an amount according to the instructions of the Glucosacn® kit (DuPont Merck, Pharmaceutical Co.) and another was formulated using a 2–3% solution of trehalose in place of tricine, each with the same amount of conjugate as the tricine formulated kit. Three control kits were formulated with the monoclonal antibody B72.3 (CYT-099) but with no linker. Each lyophilized kit was labeled with $^{99m}$Tc by adding the desired amount of pertechnetate solution to the lyophilized mixture and the combined ingredients were incubated for 20 minutes or for one hour at room temperature.

At the end of each time point, percent $^{99m}$Tc incorporation was determined. As shown in FIG. 8 only the one pot formulation of tricine, tin dichloride dihydrate and conjugate gave acceptable labeling results in 20 minutes. Further, at the end of each time point, percent of the initial $^{99m}$Tc added was determined in the colloid (% colloid, FIG. 9a); as $^{99m}$TcO$_4^-$ (% $^{99m}$TcO$_4^-$, FIG. 9b); and in the $^{99m}$Tc-transchelator complex (% 99mTc-transchelator, FIG. 9c). As shown in FIGS. 9a–c again only the one pot formulation containing tricine, tin dichloride dihydrate, and conjugate gave low levels of side-products and impurities.

6.5 $^{99m}$Tc Labeling of CYT-422

A 15 mg sample of CYT-351 antibody (mAb 7E11C5, U.S. Pat. No. 5,162,504) in phosphate buffered saline solu- The resultant conjugate mixture was stirred for 4 hours at room temperature and the product was then isolated by medium pressure chromatography on a preparative grade Superose-12 column using CBS buffer at pH 7 (10 mM citrate, 150 mM NaCl, 1 mM EDTA) as eluent. The desired eluent fractions which contained conjugate were determined by UV, combined, and concentrated on a Centraprep-30 cartridge system to a volume of approx. 2 mL. The final concentration of the CYT-422 immunoconjugate was determined by UV spectrography.

FIG. 10 demonstrates the effect of different transchelators on the efficiency of $^{99m}$Tc labeling of CYT-422. The tricine/tin kits for the radio labeling of immunoconjugate CYT-422 were prepared by mixing 500 ml of a 36 mg/ml solution of tricine, 0.5 ml of a 50 mg/ml solution of stannous dichloride dihydrate, in 1 N HCl at pH 4.86. 360 µl of 1 N NaOH was then added to bring the pH to 5.6. The resultant solution was aliquoted into 250 1 ml vials which were lyophilized. Each vial was then sealed and was ready for labeling.

$^{99m}$Tc was added to the lyophilized tricine/tin kit and subsequently the immunoconjugate CYT-422 was added and incubated for 1 hour, at room temperature. CYT-422 was also labeled with a Glucoscan® or Gluceptate® sodium glucoheptonate kit from DuPont/Merck or Mallinckrodt, Inc., respectively, according to the instructions in the commercially available kits. The efficiency of radiolabeling was determined using ITLC using saline as an eluent. The top half of the chromatography strip was cut away from the bottom half and the amount of technetium on each half was determined. Unbound radiometal was detected on the top half of the strip and immunoconjugate-bound $^{99m}$Tc was detected on the bottom half. The results show that tricine was the only transchelator that labeled the immunoconjugate satisfactorily at any given specific activity of Tc, especially at clinically significant specific activities, e.g., 50–200 mCi/mg conjugate.

6.6 One Pot Formulation of CYT-422

A one pot formulation of CYT-422 is formulated containing 10–200 mg/ml tricine, preferably 36 mg; 0.1% to 0.6% tin dichloride dihydrate, preferably 50 µg; and 0.2 to 10 mg conjugate CYT-422, preferably 1 mg, in a total volume of 1 ml and is lyophilized. The lyophilized mixture is combined with the desired amount of aqueous solution of $^{99m}$Tc radiolabel and is incubated for 5 minutes at room temperature.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A method for lyoprotecting a macromolecule comprising mixing N-[tris(hydroxymethyl)methyl]glycine with a macromolecule in an aqueous solution and lyophilizing the resulting mixture, in which the pH of the aqueous solution is a pH at which N-[tris(hydroxymethyl)methyl]glycine does not function as a buffer.

2. The method according to claim 1 in which the aqueous solution is at a pH of about 5 at which N-[tris(hydroxymethyl)methyl]glycine does not function effectively as a biological buffer.

3. The method according to claim 1 in which N-[tris(hydroxymethyl)methyl]glycine is used in excess of that used for buffering.

4. The method according to claim 3 in which N-[tris(hydroxymethyl)methyl]glycine is used at a concentration of about 10–200 mg/ml.

5. The method according to claim 3 in which N-[tris(hydroxymethyl)methyl]glycine is used at a concentration of about 18–144 mg/ml.

6. The method according to claim 1 in which the N-[tris(hydroxymethyl)methyl]glycine is present in the range of about 80% to about 99+% of the mixture.

7. The method according to claim 1 in which the N-[tris(hydroxymethyl)methyl]glycine is present in the range of about 90% to about 99+% of the mixture.

8. The method according to claim 1 in which the macromolecule is selected from the group consisting of peptides, polypeptides, proteins, glycoproteins and proteoglycans.

* * * * *